United States Patent
Inokuchi et al.

(10) Patent No.: US 9,267,037 B2
(45) Date of Patent: *Feb. 23, 2016

(54) SILICONE COMPOSITE PARTICLES, MAKING METHOD, AND COSMETIC COMPOSITION

(75) Inventors: Yoshinori Inokuchi, Annaka (JP); Ryuichi Inaba, Tokyo (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 378 days.

This patent is subject to a terminal disclaimer.

(21) Appl. No.: 12/943,166

(22) Filed: Nov. 10, 2010

(65) Prior Publication Data
US 2011/0110994 A1    May 12, 2011

(30) Foreign Application Priority Data
Nov. 11, 2009 (JP) ................................. 2009-257867

(51) Int. Cl.
| | |
|---|---|
| A61K 8/58 | (2006.01) |
| C08L 83/04 | (2006.01) |
| A61K 8/19 | (2006.01) |
| A61K 8/27 | (2006.01) |
| A61K 8/29 | (2006.01) |
| A61K 8/891 | (2006.01) |
| A61Q 15/00 | (2006.01) |
| A61Q 17/00 | (2006.01) |
| A61Q 17/04 | (2006.01) |
| C08J 3/12 | (2006.01) |
| C08G 77/12 | (2006.01) |
| C08G 77/20 | (2006.01) |

(52) U.S. Cl.
CPC . *C08L 83/04* (2013.01); *A61K 8/19* (2013.01); *A61K 8/27* (2013.01); *A61K 8/29* (2013.01); *A61K 8/891* (2013.01); *A61Q 15/00* (2013.01); *A61Q 17/005* (2013.01); *A61Q 17/04* (2013.01); *C08J 3/12* (2013.01); *C08J 3/128* (2013.01); *A61K 2800/412* (2013.01); *A61K 2800/413* (2013.01); *C08G 77/12* (2013.01); *C08G 77/20* (2013.01); *C08J 2383/04* (2013.01)

(58) Field of Classification Search
CPC ........... A61K 8/00; A61K 8/02; A61K 8/022; A61K 8/0229; A61K 8/0241; A61K 8/025; A61K 8/0258; A61K 8/0262; A61K 8/0266; A61K 8/04; A61K 8/25
USPC ........ 424/401, 489, 490, 497, 501, 65, 70.12, 424/70.121, 70.7, 70.9
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,775,452 A | 11/1973 | Karstedt | |
| 5,411,761 A | 5/1995 | Inokuchi et al. | |
| 5,538,793 A * | 7/1996 | Inokuchi et al. | 428/407 |
| 5,948,469 A | 9/1999 | Morita et al. | |
| 6,335,037 B1 * | 1/2002 | Ichinohe et al. | 424/490 |
| 6,589,561 B2 * | 7/2003 | Inokuchi et al. | 424/489 |
| 7,399,803 B2 | 7/2008 | Morita et al. | |
| 7,648,766 B2 | 1/2010 | Morita | |
| 2003/0171475 A1 * | 9/2003 | Miyazaki et al. | 524/449 |
| 2006/0054770 A1 * | 3/2006 | Lansdown | 248/349.1 |
| 2006/0058440 A1 * | 3/2006 | Morita et al. | 524/430 |
| 2007/0231355 A1 * | 10/2007 | Quadir et al. | 424/401 |
| 2008/0138621 A1 * | 6/2008 | Morita | 428/404 |

FOREIGN PATENT DOCUMENTS

| | | | | |
|---|---|---|---|---|
| EP | 0 958 805 A2 * | 5/1999 | | A61K 7/02 |
| EP | 0 958 805 A2 | 11/1999 | | |
| JP | 63-27410 A | 2/1988 | | |
| JP | 63-68513 A | 3/1988 | | |
| JP | 4-348143 A | 12/1992 | | |
| JP | 5-32914 A | 2/1993 | | |
| JP | 5-221640 A | 8/1993 | | |
| JP | 6-1709 A | 1/1994 | | |
| JP | 7-196815 A | 8/1995 | | |
| JP | 10-324817 A | 12/1998 | | |
| JP | 2001-354776 A | 12/2001 | | |
| JP | 2004-203780 A | 7/2004 | | |
| JP | 2006-188592 A | 7/2006 | | |
| WO | WO 2004/055099 A1 | 7/2004 | | |

OTHER PUBLICATIONS

European Search Report issued Mar. 2, 2011, in European Patent Application No. 10251912.

* cited by examiner

*Primary Examiner* — Michael G Hartley
*Assistant Examiner* — Micah-Paul Young
(74) *Attorney, Agent, or Firm* — Birch, Stewart, Kolasch & Birch, LLP

(57) ABSTRACT

Silicone composite particles are provided in which silicone elastomer spherical particles having a volume average particle size of 0.1-100 μm are coated with an organosilsesquioxane-based silicone resin containing inorganic nano-particles having a volume average particle size of up to 100 nm. The silicone composite particles are compounded in a cosmetic composition to exert a UV screening effect or bactericidal property inherent to inorganic nano-particles and to impart a pleasant feel on use. A preparing method and a cosmetic composition are also provided.

17 Claims, No Drawings

SILICONE COMPOSITE PARTICLES, MAKING METHOD, AND COSMETIC COMPOSITION

CROSS-REFERENCE TO RELATED APPLICATION

This non-provisional application claims priority under 35 U.S.C. §119(a) on Patent Application No. 2009-257867 filed in Japan on Nov. 11, 2009, the entire contents of which are hereby incorporated by reference.

TECHNICAL FIELD

This invention relates to silicone composite particles, a method for preparing the same, and a cosmetic composition comprising the same.

BACKGROUND ART

From the past, silicone particles are often used in cosmetic compositions for the purposes of imparting a pleasant feel on use (e.g., smooth or silky feel) and spreadability thereto. In particular, fine particles comprising spherical fine particles of silicone elastomer coated with polyorganosilsesquioxane as disclosed in JP-A H07-196815 are used in many cosmetic compositions because of soft feel, non-cohesion, and good dispersion.

The silicone particles do not possess a UV screen effect. When these particles are compounded in cosmetic compositions intended for UV screening, the particles in a cosmetic coating permit UV radiation to be transmitted thereby, detracting from the UV screening effect of the cosmetic compositions. The problem worsens particularly when silicone particles have a large particle size.

On the other hand, silicone particles which are surface coated with inorganic particles are known. For example, JP-A S63-27410 discloses spherical particles in which surfaces of thermosetting silicone resin particles are coated with titanium oxide, iron oxide or other pigments in nano-particulate form. JP-A S63-68513 discloses spherical particles in which surfaces of thermosetting silicone resin particles are coated with metal compounds, metals or other pigments in nano-particulate form. JP-A H04-348143 discloses particles in which surfaces of silicone rubber particles are coated with metal oxide in nano-particulate form. JP-A H06-001709 discloses particles in which surfaces of silicone resin particles are coated with inorganic particles. WO 2004-055099 discloses a powder in which cured silicone particles are covered with surfactant-bearing inorganic fine particles. JP-A 2006-188592 describes that silicone rubber particles are surface coated with inorganic fine particles and treated with an organosilicon compound having a silicon-bonded hydrolyzable group. Among the foregoing silicone particles, those particles having a UV screening effect are expected not to adversely affect the UV screening effect of a cosmetic composition into which they are compounded. Those particles having an antibacterial effect are expected to impart a deodorant effect to an antiperspirant cosmetic composition into which they are compounded. These silicone particles, however, are not effective for imparting a pleasant feel on use and spreadability because the particle surface is not formed of silicone.

JP-A 2006-188592 describes treatment of particles with an organosilicon compound having a silicon-bonded hydrolyzable group, which is least effective for imparting a pleasant feel on use and spreadability.

To meet the demand for particles capable of imparting a pleasant feel on use and spreadability despite the presence of inorganic particles, silicone particles containing inorganic particles therein were proposed. For example, JP-A H05-32914 discloses inorganic filler particles which are surface coated with a hydrosilylation reaction product of an organohydrogenpolysiloxane having an ethylenically unsaturated group. JP-A H05-221640 discloses titanium oxide particles which are surface coated with a hydrolytic condensate of a trialkoxysilane. JP-A H10-324817 discloses titanium oxide particles having a hydrolytic condensate of an organosilane compound applied to surfaces thereof. JP-A 2001-354776 discloses spherical particles of silicone elastomer containing titanium oxide fine particles. JP-A 2004-203780 discloses spherical particles of polyorganosilsesquioxane containing UV screening inorganic fine particles. Because of the particle surface formed of silicone and containment of inorganic particles, these particles can impart a pleasant feel on use and spreadability as well as inorganic particles' properties. However, since inorganic particles are contained within silicone particles, more inorganic particles are necessary in order to provide satisfactory properties such as a UV screening effect, giving rise to a coloring problem. In the case of silicone particles containing titanium oxide fine particles, for example, substantial loading thereof in a cosmetic composition should be avoided because the cosmetic composition otherwise becomes too white.

CITATION LIST

Patent Document 1: JP-A H07-196815
Patent Document 2: JP-A S63-27410
Patent Document 3: JP-A S63-68513
Patent Document 4: JP-A H04-348143
Patent Document 5: JP-A H06-001709
Patent Document 6: WO 2004-055099
Patent Document 7: JP-A 2006-188592
Patent Document 8: JP-A H05-32914
Patent Document 9: JP-A H05-221640
Patent Document 10: JP-A H10-324817
Patent Document 11: JP-A 2001-354776
Patent Document 12: JP-A 2004-203780

SUMMARY OF INVENTION

An object of the invention is to provide silicone composite particles which may be compounded in a cosmetic composition to impart a pleasant feel on use, such as "ease of spreading", "adhesion", "smoothness" or "softness", for example, in a cosmetic composition having a UV screening effect, to impart such a feel without detracting from the UV screening effect or in another cosmetic composition to exert a bactericidal effect inherent to inorganic particles. Another object is to provide a method for preparing the same and a cosmetic composition comprising the same.

The inventors have found that with respect to particles in the form of silicone elastomer spherical particles which are surface coated with an amount of a silicone resin, the above and other objects can be attained by incorporating inorganic nano-particles into the silicone resin. The resultant silicone composite particles may be compounded in a cosmetic composition to impart a pleasant feel on use inherent to silicone, such as "ease of spreading", "adhesion", "smoothness" or "softness". A UV screening cosmetic composition having conventional silicone composite particles compounded therein has the problem that since the silicone composite particles have a large particle size, UV radiation is transmitted by the silicone composite particles unless a substance having a UV screening effect such as titanium oxide is incorporated in the silicone composite particles. Thus the conventional UV screening cosmetic composition loses its UV screening effect. In contrast, the silicone composite particles of the invention may be compounded in a UV screening cosmetic composition to impart a pleasant feel on use inherent to silicone without detracting from the UV screening effect. They are successful in imparting not only a pleasant feel on use inherent to silicone, but also any desired property of inorganic nano-particles to the cosmetic composition. When inorganic nano-particles used have bactericidal property, for example, the silicone composite particles may be compounded in a deodorant cosmetic composition to impart a bactericidal property and a pleasant feel on use inherent to silicone.

In one aspect, the invention provides silicone composite particles comprising 100 parts by weight of spherical particles of a silicone elastomer having a volume average particle size of 0.1 to 100 μm, coated with 0.5 to 25 parts by weight of a silicone resin based on organosilsesquioxane units, the silicone resin containing inorganic nano-particles having a volume average particle size of up to 100 nm.

In a preferred embodiment, the inorganic nano-particles are selected from the group consisting of titanium oxide, iron oxide, zinc oxide and silver.

Typically the silicone composite particles have been prepared by adding an acidic or basic substance and a compound selected from the group consisting of alkoxysilanes, silanol-containing silanes and partial condensates thereof, to a mixed water dispersion of silicone elastomer spherical particles and inorganic nano-particles, and subjecting the compound to hydrolytic condensation reaction, thereby coating surfaces of the silicone elastomer spherical particles with a silicone resin having the inorganic nano-particles laden therein.

In one embodiment, the inorganic nano-particles are selected from the group consisting of titanium oxide, iron oxide, and zinc oxide, and the silicone composite particles are suited for use in UV screen cosmetics. In another embodiment, the inorganic nano-particles are of silver, and the silicone composite particles are suited for use in deodorant cosmetics.

In a second aspect, the invention provides a method for preparing the silicone composite particles, comprising the steps of adding an acidic or basic substance and a compound selected from the group consisting of alkoxysilanes, silanol-containing silanes and partial condensates thereof, to a mixed water dispersion of silicone elastomer spherical particles and inorganic nano-particles, and subjecting the compound to hydrolytic condensation reaction, thereby coating surfaces of the silicone elastomer spherical particles with a silicone resin having the inorganic nano-particles laden therein.

In a third aspect, the invention provides a cosmetic composition comprising the silicone composite particles.

One preferred embodiment is a UV screen cosmetic composition comprising silicone composite particles comprising 100 parts by weight of spherical particles of a silicone elastomer having a volume average particle size of 0.1 to 100 μm, coated with 0.5 to 25 parts by weight of a silicone resin based on organosilsesquioxane units, the silicone resin containing inorganic nano-particles of titanium oxide, iron oxide or zinc oxide having a volume average particle size of up to 100 nm.

Another preferred embodiment is a deodorant cosmetic composition comprising silicone composite particles comprising 100 parts by weight of spherical particles of a silicone elastomer having a volume average particle size of 0.1 to 100 μm, coated with 0.5 to 25 parts by weight of a silicone resin based on organosilsesquioxane units, the silicone resin containing inorganic nano-particles of silver having a volume average particle size of up to 100 nm.

Advantageous Effects of Invention

The silicone composite particles may be compounded in a cosmetic composition to exert a UV screening effect or bactericidal property inherent to inorganic nano-particles and to impart a pleasant feel on use inherent to silicone. The method is effective for preparing the silicone composite particles. A cosmetic composition comprising the silicone composite particles has many advantages.

DESCRIPTION OF EMBODIMENTS

The invention is directed to (I) silicone composite particles, (II) a method for preparing the same, and (III) a cosmetic composition comprising the same, which are described below in the order.

I. Silicone Composite Particles

The silicone composite particles are defined herein as comprising 100 parts by weight of spherical particles of a silicone elastomer having a volume average particle size of 0.1 to 100 microns (μm), which are coated with 0.5 to 25 parts by weight of a silicone resin based on organosilsesquioxane units. The silicone resin contains inorganic nano-particles having a volume average particle size of 1 to 100 nanometers (nm).

The silicone elastomer particles are generally spherical in shape and have a volume average particle size of 0.1 to 100 μm. Particles with a volume average particle size of less than 0.1 μm provide an insufficiently smooth or silky feel whereas particles with a volume average particle size of more than 100 μm tend to detract from a smooth or silky feel and sometimes produce a coarse feel. The preferred volume average particle size is in a range of 0.5 to 40 μm, and more preferably 1 to 40 μm. It is noted that the volume average particle size is determined by the electric resistance method for a size of greater than or equal to 1 μm, and by the laser diffraction method for a sub-micron size. Measurement by the electric resistance method may be done, if a sample is a water dispersion of silicone elastomer particles, by directly adding the sample to the standard electrolyte aqueous solution, and agitating for dispersion. A typical particle size distribution measuring instrument operating on the electric resistance method is Multisizer 3 by Beckman Coulter. Measurement by the laser diffraction scattering method may be done, if a sample is a water dispersion of silicone elastomer particles, by directly adding the sample to water, and agitating for dispersion. In either of the measuring methods, if a sample consists of silicone elastomer particles, it must be dispersed in water with the aid of a surfactant or water-soluble polymer, prior to measurement.

The silicone elastomer is not particularly limited in composition as long as particles thereof can produce a pleasant feel on use by virtue of inherent rubber elasticity and generally spherical shape. Where it is desired that a cosmetic composition having the silicone elastomer compounded therein exert a pleasant feel on use due to rubber elasticity, but not a sticky feel, a silicone elastomer comprising linear organosiloxane blocks having the chemical formula: —($R^1_2$ $SiO_{2/2})_n$— is preferred. Herein $R^1$ is a substituted or unsubstituted monovalent hydrocarbon group of 1 to 30 carbon atoms, and n is a positive number of 5 to 5,000.

Suitable hydrocarbon groups of $R^1$ include alkyl groups such as methyl, ethyl, propyl, butyl, pentyl, hexyl, heptyl, octyl, decyl, undecyl, dodecyl, tetradecyl, pentadecyl, hexadecyl, heptadecyl, octadecyl, nonadecyl, eicosyl, henicosyl, docosyl, tricosyl, tetrasyl, and triacosyl; aryl groups such as phenyl, tolyl and naphthyl; aralkyl groups such as benzyl and phenethyl; alkenyl groups such as vinyl and allyl; cycloalkyl groups such as cyclopentyl, cyclohexyl and cycloheptyl; and substituted forms of the foregoing in which some or all carbon-bonded hydrogen atoms are replaced by halogen atoms (e.g., fluorine, chlorine, bromine and iodine) and/or such substituents as acryloyloxy, methacryloyloxy, epoxy, glycidoxy, and carboxyl.

As used herein, the term "rubber elasticity" inherent to silicone elastomer may be represented by a rubber hardness. The preferred rubber hardness is in a range of 5 to 90 as measured by Type A Durometer according to JIS K-6253. While a hardness of less than 5 may lead to a strong cohesion, a hardness of greater than or equal to 5 provides improvements in fluidity, dispersion, smooth feel and silky touch. A hardness in excess of 90 may lead to a lack of soft feel. A rubber hardness of 10 to 80 in Type A Durometer scale is more preferred. The silicone elastomer may contain cosmetically acceptable components within its particles, such as silicone oil, organosilanes, silicone resins, inorganic particulates, organic particulates, and hydrocarbon fluids.

The silicone elastomer is generally prepared from a curable liquid silicone composition. Exemplary cure mechanisms include condensation reaction of methoxysilyl ($\equiv$SiOCH$_3$) groups with hydroxysilyl ($\equiv$SiOH) groups, radical reaction of mercaptopropylsilyl ($\equiv$Si—C$_3$H$_6$SH) groups with vinylsilyl ($\equiv$SiCH$=$CH$_2$) groups, and addition reaction of vinylsilyl ($\equiv$SiCH$=$CH$_2$) groups with hydrosilyl ($\equiv$SiH) groups. From the aspect of reactivity, a cure mechanism based on condensation reaction or addition reaction is preferred.

In an embodiment to form a silicone elastomer by curing through addition reaction, there may be used a liquid silicone composition comprising an organpolysiloxane having at least two monovalent olefinic unsaturated groups in the molecule of the average formula: $R^2_aR^3_bSiO_{(4-a-b)/2}$ in combination with an organohydrogenpolysiloxane having at least three silicon-bonded hydrogen atoms in the molecule of the average formula: $R^4_cH_dSiO_{(4-c-d)/2}$, or a liquid silicone composition comprising an organpolysiloxane having at least three monovalent olefinic unsaturated groups in the molecule of the average formula: $R^2_aR^3_bSiO_{(4-a-b)/2}$ in combination with an organohydrogenpolysiloxane having at least two silicon-bonded hydrogen atoms in the molecule of the average formula: $R^4_cH_dSiO_{(4-c-d)/2}$. In either composition, the organpolysiloxane having monovalent olefinic unsaturated groups and the organohydrogenpolysiloxane are present in such a proportion as to provide 0.5 to 2 hydrosilyl groups per monovalent olefinic unsaturated group. The liquid silicone composition may be subjected to addition polymerization in the presence of a platinum base catalyst.

In the above formula, $R^2$ is a substituted or unsubstituted, monovalent hydrocarbon group of 1 to 30 carbon atoms free of aliphatic unsaturation, and $R^3$ is a monovalent olefinic unsaturated group of 2 to 6 carbon atoms. The subscripts a and b are positive numbers in the range of $0<a<3$, $0<b\leq3$, and $0.1\leq a+b\leq3$, and preferably $0<a\leq2.295$, $0.005\leq b\leq2.3$, and $0.5\leq a+b\leq2.3$. $R^4$ is a substituted or unsubstituted, monovalent hydrocarbon group of 1 to 30 carbon atoms free of aliphatic unsaturation. The subscripts c and d are positive numbers in the range of $0<c<3$, $0<d\leq3$, and $0.1\leq c+d\leq3$, and preferably $0<c\leq2.295$, $0.005\leq d\leq2.3$, and $0.5\leq c+d\leq2.3$.

Suitable hydrocarbon groups of $R^2$ include alkyl groups such as methyl, ethyl, propyl, butyl, pentyl, hexyl, heptyl, octyl, decyl, undecyl, dodecyl, tetradecyl, pentadecyl, hexadecyl, heptadecyl, octadecyl, nonadecyl, eicosyl, henicosyl, docosyl, tricosyl, tetrasyl, and triacosyl; aryl groups such as phenyl, tolyl and naphthyl; aralkyl groups such as benzyl and phenethyl; cycloalkyl groups such as cyclopentyl, cyclohexyl and cycloheptyl; and substituted forms of the foregoing in which some or all carbon-bonded hydrogen atoms are replaced by halogen atoms (e.g., fluorine, chlorine, bromine and iodine) and/or such substituents as acryloyloxy, methacryloyloxy, epoxy, glycidoxy, and carboxyl. Preferably at least 80 mol %, more preferably at least 90 mol % of $R^2$ are non-reactive groups such as alkyl, aryl, aralkyl or cycloalkyl groups.

Suitable olefinic unsaturated groups of $R^3$ include vinyl, allyl, propenyl, butenyl, pentenyl, and hexenyl, with vinyl being preferred from the industrial aspect.

Suitable groups of $R^4$ are as exemplified for $R^2$.

Preferably the organpolysiloxane having olefinic unsaturated groups and the organohydrogenpolysiloxane each have a viscosity of lower than or equal to 100,000 mm$^2$/s, more preferably lower than or equal to 10,000 mm$^2$/s at 25° C., for the reason that if their viscosity is in excess of 100,000 mm$^2$/s at 25° C., the method to be described later is difficult to produce particles in a narrow size distribution. The organpolysiloxane having olefinic unsaturated groups and the organohydrogenpolysiloxane may have a linear, cyclic or branched structure. It is noted that the viscosity is measured at 25° C. by a capillary viscometer.

As described above, when the organpolysiloxane having olefinic unsaturated groups is used, preferred is a combination of an organpolysiloxane having at least two monovalent olefinic unsaturated groups with an organohydrogenpolysiloxane having at least three silicon-bonded hydrogen atoms, or a combination of an organpolysiloxane having at least three monovalent olefinic unsaturated groups with an organohydrogenpolysiloxane having at least two silicon-bonded hydrogen atoms. If olefinic unsaturated groups and hydrosilyl groups in their molecule are combined otherwise, the composition may sometimes fail to cure into an elastomer free of a sticky feel.

As described above, the organpolysiloxane having olefinic unsaturated groups and the organohydrogenpolysiloxane should be compounded in such a proportion as to provide 0.5 to 2 hydrogen atoms per olefinic unsaturated group. If the components are compounded in such a proportion as to provide less than 0.5 or more than 2 hydrogen atoms, then the composition may fail to cure into an elastomer free of a sticky feel or may cure into an elastomer having high reactivity. The components are preferably compounded in such a proportion as to provide 0.7 to 1.5 hydrogen atoms per olefinic unsaturated group.

The platinum base catalyst may be any of well-known catalysts. Illustrative examples include platinum group metal elements such as platinum (inclusive of platinum black), rhodium and palladium; platinum chloride, chloroplatinic acid and chloroplatinic acid salts such as H$_2$PtCl$_4$.kH$_2$O, H$_2$PtCl$_6$.kH$_2$O, NaHPtCl$_6$.kH$_2$O, KHPtCl$_6$.kH$_2$O, Na$_2$PtCl$_6$.kH$_2$O, K$_2$PtCl$_4$.kH$_2$O, PtCl$_4$.kH$_2$O, PtCl$_2$, and Na$_2$HPtCl$_4$.kH$_2$O wherein k is an integer of 0 to 6, preferably 0 or 6; alcohol-modified chloroplatinic acids as disclosed in U.S. Pat. No. 3,220,972; chloroplatinic acid-olefin complexes as disclosed in U.S. Pat. No. 3,159,601, U.S. Pat. No. 3,159,662, and U.S. Pat. No. 3,775,452; platinum group metals (e.g., platinum black and palladium) on supports (e.g., alumina, silica, carbon); rhodium-olefin complexes, chlorotris(triphenylphosphine)rhodium, known as Wilkinson catalyst; and complexes of platinum chloride, chloroplatinic acid and chloroplatinic acid salts with vinyl-bearing siloxanes, typically vinyl-bearing cyclic siloxanes.

In another embodiment to form a silicone elastomer by curing through condensation reaction, there may be used a liquid silicone composition comprising an organpolysiloxane having at least two silicon-bonded hydroxyl groups in the molecule with a siloxane having at least three silicon-bonded alkoxy groups in the molecule. The composition may be subjected to polycondensation in the presence of a condensation catalyst.

The silicone composite particles are defined herein as comprising 100 parts by weight of silicone elastomer spherical particles which are coated with 0.5 to 25 parts by weight of a silicone resin based on organosilsesquioxane units. On this basis, composite particles containing less than 0.5 part of the silicone resin become highly cohesive and poor in fluidity, dispersibility, smoothness and silky touch whereas more than 25 parts of the silicone resin detracts from a soft feel. An appropriate amount of the silicone resin is 1 to 15 parts by weight.

The silicone resin based on organosilsesquioxane units may take any form when surfaces of silicone elastomer spherical particles are coated therewith. The population or density of the silicone resin deposited on surfaces of silicone elastomer spherical particles is not particularly limited as long as the desired effect is exerted. In one embodiment, particles of the silicone resin are sparsely distributed on surfaces of silicone elastomer spherical particles. In another embodiment, particles of the silicone resin are tightly distributed on surfaces of silicone elastomer spherical particles. In a further embodiment, the silicone resin in net form (rather than particulate form) adheres to surfaces of silicone elastomer spherical particles. In a still further embodiment, the silicone resin in film form tightly covers surfaces of silicone elastomer spherical particles. Any combination of these coverage forms is also acceptable.

The silicone resin used herein is a copolymer composed mainly of organosilsesquioxane units, specifically a copolymer comprising structural units of one or more types selected from $[R^5SiO_{3/2}]$, $[R^5_2SiO_{2/2}]$, $[R^5_3SiO_{1/2}]$, and $[SiO_{4/2}]$, wherein $[R^5SiO_{3/2}]$ units are present in an amount of at least 80 mol %. Herein $R^5$ is each independently a monovalent organic group of 1 to 20 carbon atoms. For the reason that when a silicone resin is prepared by the method to be described later, specifically by hydrolytic condensation reaction of a compound selected from alkoxysilanes, silanol group-containing silanes, and partial condensates thereof, some silanol groups are left in the reaction product without undergoing condensation reaction, exactly the silicone resin is a copolymer further comprising units selected from the following structural units having a silanol group.

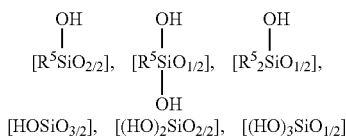

Unless structural units $[R^5SiO_{3/2}]$ or $[SiO_{4/2}]$ are incorporated, no resinous solid is available. Too high a proportion of $[SiO_{4/2}]$ may detract from smoothness. The copolymer is not particularly limited in a proportion of structural units other than $[R^5SiO_{3/2}]$, a degree of polymerization and hardness, insofar as it contains at least 80 mol % of $[R^5SiO_{3/2}]$ units, is a resinous solid at room temperature, and is insoluble in oil to be used in cosmetics (as will be described later). It is desired that $[R^5SiO_{3/2}]$ units account for at least 90 mol %. Also, if the copolymer has a low melting point, then composite particles may fuse together during storage at a high ambient temperature or drying step. Thus the copolymer preferably has a melting point of at least 50° C., more preferably at least 80° C.

Suitable hydrocarbon groups of $R^5$ include alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl; cycloalkyl groups such as cyclobutyl, cyclopentyl, cyclohexyl and cycloheptyl; aryl groups such as phenyl, tolyl and naphthyl; aralkyl groups such as benzyl, phenethyl and β-phenylpropyl; alkenyl groups such as vinyl and allyl; and substituted forms of the foregoing in which some or all carbon-bonded hydrogen atoms are replaced by halogen atoms (e.g., fluorine, chlorine, bromine and iodine) and/or such substituents as acryloyloxy, methacryloyloxy, epoxy, glycidoxy, amino, mercapto, and carboxyl. Since a resinous silicone is prepared by the method to be described later, specifically by hydrolytic condensation reaction of a compound selected from alkoxysilanes, silanol group-containing silanes, and partial condensates thereof, it is preferred for condensation reactivity that at least 50 mol %, more preferably at least 70 mol % of $R^5$ be methyl.

The silicone composite particles are characterized in that surfaces of silicone elastomer spherical particles are coated with a silicone resin which contains inorganic nano-particles.

The inorganic nano-particles used herein may be of one type or a combination of two or more types while they must be essentially acceptable for use in cosmetics. Their geometrical shape may be any of spherical, polyhedral, spindle, needle, plate and other shapes which are commonly employed in cosmetics. They may be nonporous or porous.

The inorganic nano-particles should have a volume average particle size of less than or equal to 100 nm, preferably 1 to 100 nm, and more preferably 1 to 50 nm. Inorganic nano-particles having a volume average particle size in excess of 100 nm may be poor in UV screening and bactericidal properties and sometimes cause a deeper coloring. It is noted that the volume average particle size is measured by the dynamic light scattering method. If a sample is a water dispersion of inorganic nano-particles, measurement may be done by directly adding the sample to water, and agitating for dispersion. If a sample consists of inorganic nano-particles which are dispersible in water, measurement may be done by directly adding the sample to water and agitating for dispersion. If a sample consists of inorganic nano-particles which are less dispersible in water, it must be dispersed in water with the aid of a dispersant (e.g., surfactant or water-soluble polymer), prior to measurement. A particle size on this order may be measured by submicron particle analyzer N4PLUS by Beckman Coulter.

The inorganic nano-particles may be of many various materials depending on the method and desired functions. Examples include titanium oxide, mica titanium, zirconium oxide, zinc oxide, cerium oxide, magnesium oxide, barium sulfate, calcium sulfate, magnesium sulfate, calcium carbonate, magnesium carbonate, talc, cleaved talc, mica, kaolin, sericite, white mica, synthetic mica, phlogopite, lepidolite, biotite, lithia mica, silicic acid, silicon dioxide, hydrous silicon dioxide, aluminum silicate, magnesium silicate, aluminum magnesium silicate, calcium silicate, barium silicate, strontium silicate, metal tungstates, hydroxyapatite, vermiculite, Higilite®, bentonite, montmorillonite, hectorite, zeolite, ceramics, calcium secondary phosphate, alumina, aluminum hydroxide, boron nitride, and glass.

Also included are nano-particles of inorganic pigments. Examples include inorganic red pigments such as iron oxide, iron hydroxide, and iron titanate; inorganic brown pigments such as γ-iron oxide; inorganic yellow pigments such as yellow iron oxide and ochre; inorganic black pigments such as black iron oxide and carbon black; inorganic purple pigments such as manganese violet and cobalt violet; inorganic green pigments such as chromium hydroxide, chromium oxide, cobalt oxide, and cobalt titanate; inorganic blue pigments such as Prussian blue and ultramarine; colored pigments such as lake form tar dyes and lake form natural dyes; and pearlescent pigments such as titanium oxide-coated mica, bismuth oxychloride, titanium oxide-coated bismuth oxychloride, titanium oxide-coated talc, fish scales, and titanium oxide-coated colored mica. Also included are nano-particles of metals such as aluminum, copper, stainless steel and silver.

Of the foregoing nano-particles, the preferred inorganic nano-particles having a UV screening effect include titanium oxide, iron oxide, and zinc oxide; and the preferred inorganic nano-particles having an antibacterial effect include silver and the like. While the silicone composite particles are constructed of silicone elastomer spherical particles which are surface coated with an inorganic nano-particle-laden silicone resin, surfaces of the silicone composite particles may be further treated with silylating agents, silicone oils, waxes, paraffins, organic fluorine compounds, surfactants or the like, for the purposes of imparting or improving water repellency or improving dispersion in oil.

The amount of inorganic nano-particles laden varies with the desired properties. When it is desired to impart a UV screening effect, for example, an appropriate amount is 0.1 to 25 parts by weight of inorganic nano-particles relative to 100 parts by weight of the silicone elastomer. Less than 0.1 part of inorganic nano-particles may fail to provide a sufficient UV screening effect whereas more than 25 pars of inorganic nano-particles may cause a deeper coloring, limiting the amount of the silicone composite particles compounded in cosmetic compositions. When it is desired to impart antibacterial property, even a small amount, for example, of at least $1 \times 10^{-5}$ part by weight is effective. Although the upper limit is not critical, an amount of inorganic nano-particles may be up to $1 \times 10^{-2}$ part by weight relative to 100 parts by weight of the silicone elastomer.

The silicone composite particles should preferably have a volume average particle size of 0.1 to 100 μm, more preferably 1 to 40 μm. Understandably, the measurement of a volume average particle size is the same as described for the silicone elastomer spherical particles.

II. Preparation of Silicone Composite Particles

The silicone composite particles defined herein may be prepared, for example, by a method involving adding an acidic or basic substance and a compound selected from the group consisting of alkoxysilanes, silanol-containing silanes and partial condensates thereof, to a mixed water dispersion of silicone elastomer spherical particles and inorganic nano-particles, and subjecting the compound to hydrolytic condensation reaction.

The method for preparing silicone elastomer spherical particles is not particularly limited, and any well-known methods for preparing a dispersion of silicone elastomer may be employed. For example, silicone elastomer spherical particles may be prepared by emulsifying a curable liquid silicone composition in water with the aid of a surfactant, followed by curing reaction. In an embodiment to form a silicone elastomer by curing through addition reaction, for example, one exemplary method is by adding a surfactant and water to a curable liquid silicone composition comprising an organ- polysiloxane having olefinic unsaturated groups and an organohydrogenpolysiloxane, emulsifying the mixture, adding a platinum base catalyst to the emulsion, and effecting addition polymerization.

Another exemplary method may start with a curable liquid silicone composition which has been prepared by emulsion polymerization. In another embodiment to form a silicone elastomer by curing through condensation reaction, for example, the method includes the steps of adding a surfactant and water to a cyclopolysiloxane of the general formula: $[R^6{}_2SiO]_m$ wherein $R^6$ is a substituted or unsubstituted, monovalent hydrocarbon group of 1 to 30 carbon atoms, and m is a number of 3 to 7, emulsifying the mixture, adding an acid to the emulsion, allowing polymerization reaction to run, and adding an alkali for neutralization, thereby forming an emulsion of an organopolysiloxane having a silicon-bonded hydroxyl group at either end of the linear molecule. Then an organotrialkoxysilane and a condensation catalyst are added to the emulsion to effect polycondensation.

No particular limits are imposed on the surfactant used for emulsification of the curable liquid silicone composition. Suitable surfactants include nonionic surfactants such as polyoxyethylene alkyl ethers, polyoxyethylene polyoxypropylene alkyl ethers, polyoxyethylene alkyl phenyl ethers, polyethylene glycol fatty acid esters, sorbitan fatty acid esters, polyoxyethylene sorbitan fatty acid esters, polyoxyethylene sorbitol fatty acid esters, glycerol fatty acid esters, polyoxyethylene glycerol fatty acid esters, polyglycerol fatty acid esters, propylene glycol fatty acid esters, polyoxyethylene propylene glycol fatty acid esters, polyoxyethylene castor oil, polyoxyethylene hardened castor oil, polyoxyethylene hardened castor oil fatty acid esters, polyoxyethylene phytostanol ether, polyoxyethylene phytosterol ether, polyoxyethylene cholestanol ether, polyoxyethylene cholesteryl ether, polyoxyethylene alkyl amines, alkyl alkanol amides, sucrose fatty acid esters, methylglucoside fatty acid esters, alkyl polyglucosides, linear or branched polyoxyethylene-modified organopolysiloxanes, linear or branched polyoxyethylene polyoxypropylene-modified organopolysiloxanes, polyoxyethylene/alkyl co-modified organopolysiloxanes, linear or branched polyoxyethylene polyoxypropylene/alkyl co-modified organopolysiloxanes, linear or branched polyglycerol-modified organopolysiloxanes, linear or branched polyglycerol/alkyl co-modified organopolysiloxanes, polyvinyl alcohol, polyvinyl pyrrolidone, methyl cellulose, and hydroxypropyl methyl cellulose;

anionic surfactants such as alkyl sulfuric acid ester salts, polyoxyethylene alkyl ether sulfuric acid ester salts, polyoxyethylene alkyl phenyl ether sulfuric acid ester salts, sulfuric acid ester salts of fatty acid alkylol amides, alkylbenzenesulfonic acid salts, polyoxyethylene alkyl phenyl ether sulfonic acid salts, α-olefin sulfonic acid salts, α-sulfofatty acid ester salts, alkylnaphthalene sulfonic acid salts, alkyl diphenyl ether disulfonic acid salts, alkane sulfonic acid salts, N-acyltauric acid salts, dialkylsulfosuccinic acid salts, monoalkylsulfosuccinic acid salts, polyoxyethylene alkyl ether sulfosuccinic acid salts, fatty acid salts, polyoxyethylene alkyl ether carboxylic acid salts, N-acylamino acid salts, monoalkyl phosphoric acid ester salts, dialkyl phosphoric acid ester salts, polyoxyethylene alkyl ether phosphoric acid ester salts, carboxymethyl cellulose, polyacrylic acid salts, polystyrene sulfonic acid salts, naphthalene sulfonic acid salt-formaldehyde condensates, aromatic sulfonic acid salt-formaldehyde condensates, carboxyvinyl polymers, and styrene hydroxyalkylene acid anhydride copolymers;

cationic surfactants such as alkyltrimethylammonium salts, dialkyldimethylammonium salts, polyoxyethylene alkyl dimethylammonium salts, dipolyoxyethylene alkylmethylammonium salts, tripolyoxyethylene alkylammonium salts, alkylbenzyldimethylammonium salts, alkylpyridinium salts, monoalkylamine salts, dialkylamine salts, trialkylamine salts, monoalkylamide amine salts, and cationic cellulose; and ampholytic surfactants such as alkyldimethylamine oxides, alkyldimethylcarboxybetaine, alkylamidopropyldimethylcarboxybetaine, alkylhydroxysulfobetaine, and alkylcarboxymethyl hydroxyethyl imidazolinium betaine.
These surfactants may be used alone or in admixture, and preferably in an amount of 0.1 to 50 parts by weight per 100 parts by weight of the curable liquid silicone composition.

Emulsification may be performed by ordinary emulsifying/dispersing machines. Examples include high-speed rotation centrifugal agitators such as Homodisper, high-speed rotation shear agitators such as Homomixer, high-pressure jet emulsifying/dispersing machines such as Homogenizer, colloid mills, and ultrasonic emulsifiers.

The water dispersion of silicone elastomer thus obtained is preferably used as such without solid/liquid separation. A mixed dispersion having silicone elastomer spherical particles and inorganic nano-particles dispersed in water, often referred to as simply "mixed water dispersion", may be obtained by mixing the dispersion of silicone elastomer spherical particles with inorganic nano-particles and optionally, water. The inorganic nano-particles may be used as a water dispersion prepared by previously dispersing them in water. Also preferably, a surfactant is compounded in the mixed water dispersion. Where the silicone elastomer spherical particles are prepared using a surfactant as described above, the surfactant is already present in the water dispersion of silicone elastomer spherical particles. It is sometimes preferred to further add a surfactant to the water dispersion for the purpose of uniformly coating surfaces of silicone elastomer spherical particles with the silicone resin, or incorporating inorganic nano-particles into the silicone resin so that the silicone resin is laden with inorganic nano-particles. The surfactant to be added at this stage is not particularly limited, may be selected from the above list of exemplary surfactants used for emulsification of the curable liquid silicone composition, and may be the same as or different from the surfactant contained in the water dispersion of silicone elastomer. A mixture of two or more surfactants may be added. An amount of the surfactant added to the mixed water dispersion is preferably 0.01 to 3 parts by weight per 100 parts by weight of water. Additionally, a water-soluble organic solvent may be blended.

To the mixed water dispersion, an acidic or basic substance and a compound selected from the group consisting of alkoxysilanes, silanol-containing silanes and partial condensates thereof (referred to as "silane compound", hereinafter) are added, whereby the silane compound is subjected to hydrolytic condensation reaction.

The acidic or basic substance used herein is a catalyst for hydrolytic condensation reaction of a silane compound. The acidic or basic substance is added at least to the mixed water dispersion. The order of addition is not particularly limited. In one procedure, the acidic or basic substance is first fed and a reactant(s) is then added. Another procedure is by first feeding part of a reactant(s), adding the acidic or basic substance, and adding the remaining reactant(s) in sequence.

An appropriate amount of the acidic substance added is such that the mixed water dispersion to which the acidic substance is added may have a pH level in the range of 1.0 to 4.0, more preferably 1.5 to 3.5. An amount of the acidic substance added to provide a pH level of 1.0 to 4.0 is sufficient for a silane compound to undergo hydrolytic condensation reaction.

An appropriate amount of the basic substance added is such that the mixed water dispersion to which the basic substance is added may have a pH level in the range of 10.0 to 13.0, more preferably 10.5 to 12.5. An amount of the basic substance added to provide a pH level of 10.0 to 13.0 is sufficient for a silane compound to undergo hydrolytic condensation reaction.

The acidic substance is not particularly limited. Suitable acidic substances include acid type surfactants such as alkyl sulfates and alkylbenzene sulfonic acids, carboxylic acids such as formic acid, oxalic acid, malonic acid, lactic acid and malic acid, hydrochloric acid, phosphoric acid, sulfuric acid, methanesulfonic acid, and trifluoromethanesulfonic acid.

The basic substance is not particularly limited. Suitable basic substances include alkali metal hydroxides such as potassium hydroxide, sodium hydroxide, and lithium hydroxide, alkaline earth metal hydroxides such as calcium hydroxide and barium hydroxide, alkali metal carbonates such as potassium carbonate and sodium carbonate, ammonia, tetraalkylammonium hydroxides such as tetramethylammonium hydroxide and tetraethylammonium hydroxide, and amines such as monomethylamine, monoethylamine, monopropylamine, monobutylamine, monopentylamine, dimethylamine, diethylamine, trimethylamine, triethanolamine, and ethylene diamine.

Among others, ammonia is most preferred because it can be readily removed from the resultant silicone particle powder by volatilization. Commercially available ammonia water may be used as the ammonia.

Under the catalysis of the acidic or basic substance, a silane compound undergoes hydrolytic condensation reaction, forming a silicone resin within the scope of the invention.

The alkoxysilanes used herein include those of general formulae: $R^5Si(OR^7)_3$, $R^5{}_2Si(OR^7)_2$, $R^5{}_3SiOR^7$, and $Si(OR^7)_4$ wherein $R^5$ is as defined above and $R^7$ is an unsubstituted monovalent hydrocarbon group of 1 to 6 carbon atoms. Exemplary groups of $R^7$ include methyl, ethyl, propyl, butyl, pentyl, and hexyl, with methyl being preferred for reactivity. The alkoxysilanes: $R^5Si(OR^7)_3$, $R^5{}_2Si(OR^7)_2$, $R^5{}_3SiOR^7$, and $Si(OR^7)_4$ are sources to structural units $[R^5SiO_{3/2}]$, $[R^5{}_2SiO_{2/2}]$, $[R^5{}_3SiO_{1/2}]$, and $[SiO_{4/2}]$ of silicone resin, respectively. Accordingly, a blending proportion of $R^5Si(OR^7)_3$, $R^5{}_2Si(OR^7)_2$, $R^5{}_3SiOR^7$, and $Si(OR^7)_4$ may be determined so as to yield a silicone resin of the desired structure. That is, a molar ratio of $R^5Si(OR^7)_3:R^5{}_2Si(OR^7)_2:R^5{}_3SiOR^7:Si(OR^7)_4$ may be determined to be equal to the desired molar ratio of structural units $[R^5SiO_{3/2}]:[R^5{}_2SiO_{2/2}]:[R^5{}_3SiO_{1/2}]:[SiO_{4/2}]$. As described above, the silicone resin is composed mainly of organosilsesquioxane units, and specifically comprises at least 80 mol %, more preferably at least 90 mol % of $[R^5SiO_{3/2}]$ units.

The silanol-containing silanes used herein correspond to the alkoxysilanes of the above general formulae wherein $R^7$ is hydrogen. A proper choice may be made among alkoxysilanes, silanol-containing silanes, and condensates thereof so as to yield the desired structural units.

With stirring, a silane compound is added to a water dispersion containing at least silicone elastomer spherical particles, inorganic nano-particles, and an acidic or basic substance, whereupon hydrolytic condensation reaction takes place. The silane compound may be slowly added dropwise, added as a solution or dispersion in water, or added as a blend with a water-soluble organic solvent such as alcohol. As hydrolytic condensation reaction proceeds, a silicone resin forms while taking inorganic nano-particles therein and covering surfaces of the silicone elastomer. There are formed composite particles in the form of silicone elastomer spherical particles which are surface coated with the inorganic nano-particle-laden silicone resin.

With respect to the agitation for resin formation and coating, the agitating speed is not particularly limited as long as the silane compound is dispersed in the water dispersion. Strong agitation may cause particles to agglomerate together. In such a case, mild agitation using paddle, propeller, retreat, anchor and other impellers may be adequate.

When the silane compound is added to the mixed water dispersion, the temperature is preferably in a range of 0 to 60° C., more preferably 0 to 39° C. Temperatures below 0° C. may cause the water dispersion to solidify whereas temperatures above 60° C. may cause the resulting particles to agglomerate together.

An alternative method which may be employed herein is by adding the silane compound to the mixed water dispersion which has been adjusted neutral or weakly acidic, agitating the mixture until hydrolysis takes place, then adding a basic substance, and holding the mixture, thus allowing condensation reaction to take place.

When it is desired that particles be surface treated with a silylating agent, the silicone composite particles finished as above may be so treated. Alternatively, after the silane compound is added to the mixed water dispersion, a silylating agent may be added to effect the desired treatment. Suitable silylating agents used herein include dimethyldichlorosilane, trimethylchlorosilane, trimethylmethoxysilane, trimethylsilanol-containing silanes, and hexamethyldisilazane.

It is preferred to continue agitation for a certain time from the end of addition of the silane compound to the completion of hydrolysis and condensation reaction. The reaction may be promoted by heating at a temperature of 40 to 100° C. or by feeding an additional portion of the acidic or basic substance. Thereafter, a basic or acidic substance may be added to the reaction system for neutralization, if necessary.

After the completion of hydrolysis and condensation reaction, the water is removed. Water removal may be done, for example, by heating the reacted water dispersion under atmospheric or subatmospheric pressure. More specifically, water may be removed by statically holding the dispersion at elevated temperature, by agitating the dispersion at elevated temperature for fluidizing the dispersion, by spraying the dispersion into a hot air stream by a spray dryer or the like, or by utilizing a flowing heat medium. Prior to the step of water removal, the dispersion may be concentrated by suitable means such as heat drying, filter separation such as pressure filtration, centrifugal separation, or decantation, and if necessary, the dispersion may be washed with water, alcohol or the like.

Water removal from the reacted water dispersion yields a powder of silicone composite particles. If the powder is in agglomerated form, it may be disintegrated using a grinding machine such as a jet mill, ball mill or hammer mill, or classified.

III. Cosmetic Composition Comprising Silicone Composite Particles

The silicone composite particles defined herein (referred to as component (A)) may be used in a variety of cosmetics. They find a better use in cosmetics externally applied to the skin and hair, for example, skin care products, makeup products, hair care products, deodorant products, and UV screen products. The amount and combination of the silicone composite particles are not particularly limited. An appropriate amount may be selected in the range of 0.1 to 95.0% by weight based on the total cosmetic composition, depending on a particular formulation. The amount may be generally in a range of 0.1 to 20.0%, preferably 0.5 to 10.0% by weight, when used in UV screen cosmetic compositions. The amount may be generally in a range of 0.001 to 20.0%, preferably 0.1 to 10.0% by weight, when used in deodorant cosmetic compositions. In addition to the silicone composite particles (A), various components commonly used in ordinary cosmetics may be compounded in the cosmetic composition insofar as the benefits of the invention are not impaired. Suitable components include, for example, (B) an oil, (C) water, (D) an alcoholic hydroxyl-containing compound, (E) a water-soluble or water-swellable polymer, (F) particles other than the silicone composite particles, (G) a surfactant, (H) a composition consisting of a crosslinkable organopolysiloxane and a normally liquid oil, (I) a silicone resin, (J) a silicone wax, and other additives. Each of these components may be used alone or in admixture of two or more species.

Component (B) is an oil or fat which may be solid, semi-solid, or liquid. Use may be made of natural animal and vegetable oils and fats, semi-synthetic oils and fats, hydrocarbon oils, higher alcohols, ester fluids, silicone fluids, and fluorinated fluids, for example.

Examples of natural animal and vegetable oils and fats, semi-synthetic oils and fats include avocado oil, linseed oil, almond oil, insect wax, perilla oil, olive oil, cacao fat, kapok wax, kaya oil, carnauba wax, liver oil, candelilla wax, purified candelilla wax, beef tallow, beef foot oil, beef bone fat, hardened beef tallow, apricot kernel oil, spermaceti, hydrogenated oil, wheat germ oil, sesame oil, rice germ oil, rice bran oil, sugar cane wax, sasanqua oil, safflower oil, shea butter, tung oil, cinnamon oil, jojoba oil, squalane, squalene, shellac wax, turtle oil, soybean oil, tea seed oil, tsubaki oil, primrose oil, corn jerm oil, lard, canola oil, Japanese tung oil, rice bran wax, germ oil, horse oil, persic oil, palm oil, palm kernel oil, castor oil, hardened castor oil, castor oil fatty acid methyl ester, sunflower oil, grape seed oil, bayberry wax, jojoba oil, macadamia nut oil, bees wax, mink oil, meadowfoam oil, cotton seed oil, cotton wax, Japan haze wax, Japan haze kernel oil, montan wax, coconut oil, hardened coconut oil, tri(coconut oil fatty acid) glyceride, mutton tallow, peanut oil, lanolin, liquid lanolin, reduced lanolin, lanolin alcohol, hard lanolin, acetic acid lanolin, acetic acid lanolin alcohol, lanolin fatty acid isopropyl, polyoxyethylene lanolin alcohol ester, polyoxyethylene lanolin alcohol acetate, lanolin fatty acid polyethylene glycol, polyoxyethylene hydrogenated lanolin alcohol ester, and egg oil.

Examples of the hydrocarbon oils include linear, branched and volatile hydrocarbon oils such as ozokerite, α-olefin oligomers, light isoparaffin, isododecane, isohexadecane, light liquid isoparaffin, squalane, synthetic squalane, vegetable squalane, squalene, ceresin, paraffin, paraffin wax, polyethylene wax, polyethylene-polypropylene wax, ethylene/propylene/styrene copolymers, butylene/propylene/styrene copolymers, liquid paraffin, liquid isoparaffin, pristane, polyisobutylene, hydrogenated polyisobutene, microcrystalline wax, vaseline, etc.; higher fatty acids such as lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, etc.

Exemplary higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecinol, cholesterol, phytosterol, polyoxyethylene cholesterol ether, monostearyl glycerol ether (batyl alcohol), monooleyl glycerol ether (selachyl alcohol), etc.

Exemplary ester fluids include diisobutyl adipate, 2-hexyldecyl adipate, di-2-heptylundecyl adipate, N-alkylglycol monoisostearate, isocetyl isostearate, trimethylolpropane monoisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dioctanoate, neopentyl glycol dicaprylate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, N-lauroyl-L-glutamic acid 2-octyldedecyl ester, lauroylsarcosine isopropyl ester, diisostearyl malate, etc.; and glyceride oils such as acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, diglyceryl myristate isostearate, etc.

Suitable silicone fluids include low to high viscosity linear or branched organopolysiloxanes such as dimethylpolysiloxane, tristrimethylsiloxymethylsilane, caprylyl methicone, phenyl trimethicone, tetrakistrimethylsiloxysilane, methylphenylpolysiloxane, methylhexylpolysiloxane, methylhydrogenpolysiloxane, and dimethylsiloxane-methylphenylsiloxane copolymers; cyclic organopolysiloxanes such as octamethylcyclotetrasiloxane, decamethylcyclopentasiloxane, dodecamethylcyclohexasiloxane, tetramethyltetrahydrogencyclotetrasiloxane, and tetramethyltetraphenylcyclotetrasiloxane; silicone rubbers such as amino-modified organopolysiloxane, pyrrolidone-modified organopolysiloxane, pyrrolidone carboxylic acid-modified organopolysiloxane, gum-like dimethylpolysiloxane having a high degree of polymerization, gum-like amino-modified organopolysiloxane, gum-like dimethylsiloxane-methylphenylsiloxane copolymers; cyclic organopolysiloxane solutions of silicone gum or rubber, cyclic siloxane solutions of trimethylsiloxysilicic acid and trimethylsiloxysilicic acid, higher alkoxy-modified silicones such as stearoxysilicone, higher fatty acid-modified silicones, alkyl-modified silicones, long chain alkyl-modified silicones, amino acid-modified silicones, fluorine-modified silicones, silicone resins and molten silicone resins.

Suitable fluorinated fluids include perfluoropolyether, perfluorodecalin, and perfluorooctane.

An appropriate amount of oil (B) may be selected in the range of 1 to 98% by weight based on the total cosmetic composition, depending on a particular formulation.

An appropriate amount of water (C) may be selected in the range of 1 to 95% by weight based on the total cosmetic composition, depending on a particular formulation.

Examples of the alcoholic hydroxyl-containing compound (D) include lower alcohols such as ethanol and isopropanol, and sucrose alcohols such as sorbitol and maltose. Also included are sterols such as cholesterol, sitosterol, phytosterol, and lanosterol, and polyhydric alcohols such as butylene glycol, propylene glycol, dibutylene glycol, and pentylene glycol. An appropriate amount of compound (D) may be selected in the range of 0.1 to 98% by weight based on the total cosmetic composition.

Examples of the water-soluble or water-swellable polymer (E) include vegetable-derived polymers such as gum arabic, tragacanth, galactan, carob gum, gua gum, karaya gum, carrageenan, pectin, agar, quince seed gum, starch (of rice, corn, potato, wheat, etc.), algae colloid, trant gum, and locust bean gum; microorganism-derived polymers such as xanthane gum, dextran, succinoglucan, and pullulan; animal-derived polymers such as collagen, casein, albumin, and gelatin; starch based polymers such as carboxymethyl starch and methylhydroxypropyl starch; cellulosic polymers such as methyl cellulose, ethyl cellulose, methylhydroxypropyl cellulose, carboxymethyl cellulose, hydroxymethyl cellulose, hydroxypropyl cellulose, nitrocellulose, cellulose sodium sulfate, sodium carboxymethyl cellulose, crystalline cellulose, and cellulose powder; sodium alginate and alginic acid based polymers such as alginic acid propylene glycol ester; vinyl polymers such as polyvinyl methyl ether and carboxyvinyl polymers; acrylic polymers such as polyoxyethylene base polymers, polyoxyethylene polyoxypropylene copolymers, sodium polyacrylate, polyethyl acrylate, polyacrylamide, and acryloyl dimethyl taurine salt copolymers; synthetic water-soluble polymers such as polyethylene imine and cationic polymers; and inorganic water-soluble polymers such as bentonite, aluminum magnesium silicate, montmorillonite, beidellite, nontronite, saponite, hectolite, and silicic acid anhydride. Also included in the water-soluble polymers are film-forming polymers such as polyvinyl alcohol and polyvinyl pyrrolidone. An appropriate amount of polymer (E) may be selected in the range of 0.1 to 25% by weight based on the total cosmetic composition.

Examples of particles (F) other than the silicone composite particles include inorganic particles, organic particles, inorganic/organic composite powders, and silicone resin particles. Suitable inorganic particles are the same as previously exemplified for the inorganic nano-particles used herein. Suitable organic particles include polyamide, polyacrylic acid-acrylate, polyester, polyethylene, polypropylene, polystyrene, styrene-acrylic acid copolymers, divinylbenzene-styrene copolymers, polyurethane, vinyl resins, urea resins, melamine resins, benzoguanamine, polymethylbenzoguanamine, tetrafluoroethylene, polymethyl methacrylate, cellulose, silk, nylon, phenolic resins, epoxy resins, and polycarbonate, in powder form.

Also included are surface active metal salts (metal soaps) in powder form. Exemplary are zinc stearate, aluminum stearate, calcium stearate, magnesium stearate, zinc myristate, magnesium myristate, zinc cetylphosphate, calcium cetylphosphate, and zinc sodium cetylphosphate.

Further included are organic dyes, examples of which include tar dyes such as Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, and Orange #207; and natural dyes such as carmic acid, laccaic acid, carthamin, brazilin and crocin.

The inorganic/organic composite powders used herein may be composite powders in which surfaces of inorganic powder particles commonly used in cosmetics are covered with organic powder particles by any well-known methods.

The silicone resin particles used herein include silicone elastomer particles, polymethylsilsesquioxane particles, and silicone elastomer particles which are surface coated with polymethylsilsesquioxane. These powders (particles) may be surface treated with silylating agents, silicone fluids, waxes, paraffins, organic fluorine compounds, and surfactants prior to use.

Component (G) is a surfactant. Suitable surfactants include nonionic, anionic, cationic and ampholytic surfactants, examples of which are the same as previously enumerated in conjunction with the preparation of the silicone composite particles. Preferred among others are linear or branched polyoxyethylene-modified organopolysiloxane, linear or branched polyoxyethylene polyoxypropylene-modified organopolysiloxane, linear or branched polyoxyethylene/alkyl co-modified organopolysiloxane, linear or branched polyoxyethylene polyoxypropylene/alkyl co-modified organopolysiloxane, linear or branched polyglycerol-modified organopolysiloxane, and linear or branched polyglycerol/alkyl co-modified organopolysiloxane. In these surfactants, hydrophilic polyoxyethylene, polyoxyethylene polyoxypropylene or polyglycerol residues preferably account for 10 to 70% by weight of the molecule. An appropriate amount of surfactant (G) may be selected in the range of 0.1 to 20% by weight, more preferably 0.2 to 10% by weight based on the total cosmetic composition. The surfactant preferably has a HLB in the range of 2 to 14.5, but is not limited thereto.

Component (H) is a composition consisting essentially of a crosslinkable organopolysiloxane and a normally liquid oil. Preferably the crosslinkable organopolysiloxane swells by containing the liquid oil in an amount of more than or equal to its own weight. The oil which is liquid at room temperature may be any of liquid silicone oils, hydrocarbon oils, ester oils, natural animal and vegetable oils, semi-synthetic oils, and fluorinated oils, listed as component (B). Exemplary are low viscosity silicone oils, specifically having a viscosity of 0.65 $mm^2/s$ to 100.0 $mm^2/s$ at 25° C., hydrocarbon oils such as liquid paraffin, squalane, isododecane, and isohexadecane, glyceride oils such as trioctanoin, ester oils such as isotridecyl isononanoate, N-acylglutamic acid esters, sarcosine lauroyl ester, and vegetable oils such as macadamia nut oil. A crosslinker for the crosslinkable organopolysiloxane is preferably a compound which has at least two vinyl reactive sites in the molecule and reacts with silicon-bonded hydrogen atoms to form a crosslinked structure. Suitable compounds having at least two vinyl reactive sites in the molecule include organopolysiloxanes having at least two vinyl groups in the molecule, polyoxyalkylenes having at least two allyl groups in the molecule, polyglycerols having at least two allyl groups in the molecule, and $\alpha,\omega$-alkenyl diene. Also useful is a crosslinkable organopolysiloxane containing in the crosslinking molecule at least one moiety selected from the group consisting of a polyoxyalkylene moiety, polyglycerol moiety, long-chain alkyl moiety, alkenyl moiety, aryl moiety, and fluoroalkyl moiety. The composition consisting essentially of a crosslinkable organopolysiloxane and a normally liquid oil (H) may be compounded in an amount of 0.1 to 80% by weight, more preferably 1 to 50% by weight based on the total cosmetic composition.

Component (H) is a silicone resin, preferably an acrylic silicone resin in the form of an acrylic/silicone graft or block copolymer. Also useful are acrylic silicone resins containing in the molecule at least one member selected from the group consisting of a pyrrolidone moiety, long-chain alkyl moiety, polyoxyalkylene moiety, fluoroalkyl moiety, and anionic moiety (e.g., carboxylic acid). Further the silicone resin is preferably a silicone reticulated compound comprising a resin composed of $R^8{}_3SiO_{0.5}$ units and $SiO_2$ units, a resin composed of $R^8{}_3SiO_{0.5}$ units, $R^8{}_2SiO$ units and $SiO_2$ units, a resin composed of $R^8{}_3SiO_{0.5}$ units and $R^8SiO_{1.5}$ units, a resin composed of $R^8{}_3SiO_{0.5}$ units, $R^8{}_2SiO$ units and $R^8SiO_{1.5}$, or a resin composed of $R^8{}_3SiO_{0.5}$ units, $R^8{}_2SiO$ units, $R^8SiO_{1.5}$, and $SiO_2$ units. Herein $R^8$ is a substituted or unsubstituted, monovalent hydrocarbon group of 1 to 30 carbon atoms. Also useful is a silicone reticulated compound comprising in the molecule at least one moiety selected from the group consisting of a pyrrolidone moiety, long-chain alkyl moiety, polyoxyalkylene moiety, polyglycerol moiety, fluoroalkyl moiety, and amino moiety. When a silicone resin such as an acrylic silicone resin or silicone reticulated compound is used, an appropriate amount is 0.1 to 20% by weight, more preferably 1 to 10% by weight based on the total cosmetic composition.

Component (J) is a silicone wax, preferably an acrylic silicone resin in the form of an acrylic/silicone graft or block copolymer. Also useful are acrylic silicone resins containing in the molecule at least one member selected from the group consisting of a pyrrolidone moiety, long-chain alkyl moiety, polyoxyalkylene moiety, fluoroalkyl moiety, and anionic moiety (e.g., carboxylic acid). Also preferably the silicone wax is a polylactone-modified polysiloxane, i.e., polysiloxane having attached thereto a polylactone which is a ring-opening polymerization product of a lactone compound having a five or more membered ring. Further the silicone wax may be a silicone-modified olefin wax obtained from addition reaction of an unsaturated group-containing olefin wax consisting of an $\alpha$-olefin and a diene, with an organohydrogenpolysiloxane having at least one SiH bond in the molecule. In the olefin wax, preferred $\alpha$-olefins are those of 2 to 12 carbon atoms such as ethylene, propylene, 1-butene, 1-hexene, and 4-methyl-1-pentene, and preferred diens include butadiene, isoprene, 1,4-hexadiene, vinyl norbornene, ethylidene norbornene, and dicyclopentadiene. The organohydrogenpolysiloxane having a SiH bond may be of a linear or siloxane branched structure.

Other additives which can be used herein include oil-soluble gelling agents, antiperspirants, UV absorbers, UV absorbing/scattering agents, humectants, antibacterial agents, preservatives, perfumes, salts, antioxidants, pH modifying agents, chelating agents, refreshing agents, antiinflammatory agents, skin modifying agents (e.g., whitening agents, cell activating agents, rough skin preventing agents, blood flow stimulants, astringents, antiseborrheic agents), vitamins, amino acids, nucleic acids, hormones, inclusions, and hair setting agents.

Suitable oil-soluble gelling agents include metal soaps such as aluminum stearate, magnesium stearate, and zinc myristate; amino acid derivatives such as N-lauroyl-L-glutamic acid and $\alpha,\gamma$-di-n-butylamine; dextrin fatty acid esters such as dextrin palmitate, dextrin stearate, and dextrin 2-ethylhexanoic acid palmitic acid ester; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; organic modified clay minerals such as dimethylbenzyldodecylammonium montmorillonite clay and dimethyldioctadecylammonium montmorillonite clay.

Suitable antiperspirants include aluminum chlorohydrate, aluminum chloride, aluminum sesquichlorohydrate, zirconium hydrochloride, aluminum zirconium hydrochloride, and aluminum zirconium glycine complex.

Suitable UV absorbers include benzoic acid base UV absorbers such as p-aminobenzoic acid; anthranilic acid base UV absorbers such as methyl anthranilate; salicylic acid base UV absorbers such as methyl salicylate, octyl salicylate and trimethylcyclohexyl salicylate; cinnamic acid base UV absorbers such as octyl p-methoxycinnamate; benzophenone base UV absorbers such as 2,4-dihydroxybenzophenone; urocanic acid base UV absorbers such as ethyl urocanate; dibenzoylmethane base UV absorbers such as 4-t-butyl-4'-methoxy-dibenzoylmethane; phenylbenzimidazole sulfonic acid, triazine derivatives, etc. Suitable UV absorbing/scattering agents are particles capable of absorbing and scattering UV, for example, microparticulate titanium oxide, microparticulate iron-containing titanium oxide, microparticulate zinc oxide, microparticulate cerium oxide, and composites thereof. Also useful is a dispersion of UV absorbing/scattering particles in oil.

Suitable humectants include glycerol, glycerol condensates such as diglycerol, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate, polyoxyethylene methyl glucoside, polyoxypropylene methyl glucoside, egg lecithin, soybean lecithin, phosphatidyl choline, phosphatidyl ethanolamine, phosphatidyl serine, phosphatidyl glycerol, phosphatidyl inositol, and sphingolipid.

Suitable antibacterial preservatives include p-hydroxybenzoic acid alkyl esters, benzoic acid, sodium benzoate, sorbic acid, potassium sorbate, and phenoxyethanol. Suitable antibacterial agents include benzoic acid, salicylic acid, carbolic acid, sorbic acid, p-hydroxybenzoic acid alkyl esters, p-chloro-m-cresol, hexachlorophene, benzalkonium chloride, chlorohexidine chloride, trichlorocarbanilide, photosensitive dyes, and phenoxy ethanol.

Suitable salts include inorganic salts, organic acid salts, amine salts and amino acid salts. Exemplary of inorganic salts are sodium, potassium, magnesium, calcium, aluminum, zirconium, and zinc salts of mineral acids such as hydrochloric acid, sulfuric acid, carbonic acid and nitric acid. Exemplary of organic acid salts are salts of organic acids such as acetic acid, dehydroacetic acid, citric acid, malic acid, succinic acid, ascorbic acid, and stearic acid. Exemplary of amine salts and amino acid salts are salts of amines such as triethanolamine and salts of amino acids such as glutamic acid. Also useful are hyaluronic acid, chondroitin sulfate and other salts, and aluminum zirconium glycine complex, as well as neutralized acid-alkali salts commonly used in cosmetic formulations.

Suitable antioxidants include tocopherol, p-t-butylphenol, butylhydroxyanisole, dibutylhydroxytoluene, and phytic acid. Suitable pH modifiers include lactic acid, citric acid, glycolic acid, succinic acid, tartaric acid, dl-malic acid, potassium carbonate, sodium hydrogen carbonate, ammonium hydrogen carbonate, etc. Suitable chelating agents include alanine, sodium EDTA, sodium polyphosphate, sodium metaphosphate, and phosphoric acid. Suitable refreshing agents include L-menthol and camphor. Suitable antiinflammatory agents include allantoin, glycyrrhizic acid and salts thereof, glycyrrhetinic acid, stearyl glycyrrhetinate, tranexamic acid, and azulene.

Suitable skin modifying agents include whitening agents such as placenta extract, arbutin, glutathione, and saxifraga sarmentosa extract; cell activating agents such as royal jelly, photosensitive dyes, cholesterol derivatives and calf blood extract; rough skin modifying agents; blood flow stimulants such as nonanoic acid valenylamide, nicotinic acid benzyl ester, nicotinic acid β-butoxyethyl ester, capsaicin, jingeron, cantharis tincture, ichthammol, caffeine, tannic acid, α-borneol, nicotinic acid tocopherol, inositol hexanicotinate, cyclandelate, cinnalysine, tolazoline, acetylcholine, verapamil, cepharanthine, and γ-oryzanol; astringents such as zinc oxide and tannic acid; antiseborrheic agents such as sulfur and thianthol.

Suitable vitamins include vitamin A such as vitamin A oil, retinol, retinol acetate, and retinol palmitate; vitamin B2 such as riboflavin, riboflavin butyrate, and flavin adenine nucleotide; vitamin B6 such as pyridoxine hydrochloride, pyridoxine dioctanoate, and pyridoxine tripalmitate; vitamin B such as vitamin B12 and derivatives thereof, vitamin B15 and derivatives thereof; vitamin C such as L-ascorbic acid, L-ascorbic acid dipalmitic acid ester, L-ascorbic acid-2-sodium sulfate, and L-ascorbic acid phosphoric acid diester dipotassium; vitamin D such as ergocalciferol and cholecalciferol; vitamin E such as α-tocopherol, β-tocopherol, γ-tocopherol, dl-α-tocopherol acetate, dl-α-tocopherol nicotinate, and dl-α-tocopherol succinate; nicotinic acid derivatives such as nicotinic acid, nicotinic acid benzyl, and nicotinic acid amide; pantothenic acids and biotins such as vitamin H, vitamin P, calcium pantothenate, D-pantothenyl alcohol, pantothenyl ethyl ether, and acetylpantothenyl ethyl ether.

Suitable amino acids include glycine, valine, leucine, isoleucine, serine, threonine, phenylalanine, arginine, lysine, aspartic acid, glutamic acid, cystine, cysteine, methionine, and tryptophan. A typical nucleic acid is deoxyribonucleic acid. Suitable hormones include estradiol and ethenyl estradiol.

Suitable hair setting agents include ampholytic, anionic, cationic and nonionic polymers, for example, vinyl pyrrolidone base polymers such as polyvinyl pyrrolidone and vinyl pyrrolidone/vinyl acetate copolymers, acidic vinyl ether base polymers such as methyl vinyl ether/maleic anhydride alkyl half ester copolymers, acidic vinyl acetate polymers such as vinyl acetate/crotonic acid copolymers, acidic acrylic polymers such as (meth)acrylic acid/alkyl(meth)acrylate copolymers and (meth)acrylic acid/alkyl(meth)acrylate/alkyl acrylamide copolymers, and ampholytic acrylic polymers such as N-methacryloylethyl-N,N-dimethyl-ammonium α-N-methylcarboxybetain/alkyl(meth)acrylate copolymers, hydroxypropyl(meth)acrylate/butylaminoethyl methacrylate/ acrylic acid octyl amide copolymers. Also advantageously naturally occurring polymers such as cellulose or derivatives thereof, keratin and collagen or derivatives thereof may be used.

The cosmetic composition may take the form of powder, oil, water-in-oil type emulsion, oil-in-water type emulsion, non-aqueous emulsion, or multi-emulsion such as W/O/W or O/W/O. Also it may be of liquid, milky emulsion, cream, solid, paste, gel, powder, pressed, multilayer, mousse, spray, stick, pencil or other form. Exemplary cosmetic compositions include skin care cosmetic products such as toilet water, milky emulsion, cream, cleansing agent, pack, oil liquid, massage cream, cosmetic liquid, cosmetic oil, detergent, deodorant, hand cream, lip cream, and anti-wrinkle agent; makeup cosmetic products such as makeup foundation, concealer, cosmetic powder, powder foundation, liquid foundation, cream foundation, oily foundation, blusher, eye shadow, mascara, eye liner, eye blow, and lip stick; hair care cosmetic products such as shampoo, rinse, treatment and setting agent; deodorant products such as antiperspirant and body deodorant; and UV screen cosmetic products such as sun-screen oil, sun care milk (sun-screen milky emulsion), and sun-screen cream. In the embodiment wherein inorganic nano-particles having a UV screening effect such as titanium oxide, iron oxide or zinc oxide are used, the silicone composite particles are advantageously used in UV screen cosmetic compositions, and cosmetic compositions having these silicone composite particles compounded therein are effective as UV screening cosmetic products. In the embodiment wherein silver having a bactericidal effect is used, the silicone composite particles are advantageously used in deodorant cosmetic compositions, and cosmetic compositions having these silicone composite particles compounded therein are effective as deodorant cosmetic products.

The cosmetic compositions may be any of various forms including liquid, milky emulsion, cream, solid, paste, gel, powder, pressed, multilayer, mousse, spray, stick, and pencil forms.

EXAMPLE

Examples and Comparative Examples are shown below by way of illustration and not by way of limitation. All parts are by weight. The measurement of volume average particle size is as described above. A viscosity ($mm^2/s$) is measured at 25° C.

Example 1

Titanium Oxide-Laden Silicone Resin-Coated Silicone Elastomer Composite Particles A glass beaker having a volume of 1 liter was charged with 50 g of methylvinylpolysiloxane of formula (1) having a viscosity of 580 $mm^2/s$ and 19 g of methylhydrogenpolysiloxane of formula (2) having a viscosity of 30 $mm^2/s$ (to give 1.06 hydrosilyl groups per olefinic unsaturated group). Using a homomixer, the ingredients were agitated at 2,000 rpm and dissolved. Then 3 g of polyoxyethylene lauryl ether (molar amount of ethylene oxide added=9 moles) and 55 g of water were added. Using a homomixer, the ingredients were agitated at 6,000 rpm whereupon an oil-in-water type emulsion was formed and a viscosity buildup was observed. Agitation was continued for a further 15 minutes. While agitating at 2,000 rpm, 421 g of water was added to the emulsion which turned into a uniform white emulsion. The emulsion was transferred into a 1-liter glass flask equipped with an agitator having an anchor shaped impeller where it was conditioned at a temperature of 15-20° C. With stirring, a mixed solution of 0.8 g of a toluene solution of chloroplatinic acid-olefin complex (platinum content 0.5 wt %) and 1.6 g of polyoxyethylene lauryl ether (molar amount of ethylene oxide added=9 moles) was added to the flask. Stirring was continued for 12 hours at the temperature, yielding a water dispersion of silicone elastomer fine particles. On observation of silicone elastomer fine particles under an optical microscope, they were spherical. A particle size distribution was measured by instrument Multisizer 3 (Beckman Coulter), finding a volume average particle size of 5 μm.

The water dispersion of silicone elastomer spherical particles, 867 g, was transferred into a 3-liter glass flask equipped with an agitator having an anchor shaped impeller, to which were added 153 g of a water dispersion of titanium oxide nano-particles (trade name, Sunveil PW-6030A-20, by Catalysts and Chemicals Industries Co., Ltd., titanium oxide concentration 21 wt %, average particle size 60 nm) (to give 7.1 parts of titanium oxide per 100 parts of silicone elastomer spherical particles), 1,865 g of water and 57 g of 28 wt % ammonia water. At this point, the liquid was at pH 11.3. After it was conditioned at 5-10° C., a mixture of 54 g of methyltrimethoxysilane and 4 g of γ-aminopropyltrimethoxysilane (to give 6.5 parts of polyorganosilsesquioxane per 100 parts of silicone elastomer spherical particles after hydrolytic condensation reaction) was added dropwise over 20 minutes. While the liquid was maintained at a temperature of 5-10° C., agitation was continued for a further 1 hour. The liquid was then heated at 55-60° C. At the temperature, agitation was continued for 1 hour for bringing hydrolytic condensation reaction between methyltrimethoxysilane and γ-aminopropyltrimethoxysilane to completion.

After the hydrolytic condensation reaction, the liquid was filtered and dehydrated using a pressure filter holder with a filter paper (trade name, quantitative filter paper No. 5C, Advantec Toyo Kaisha, Ltd., retaining particle size 1 μm). The dehydrated mass was transferred into a 5-liter glass flask equipped with an agitator having an anchor shaped impeller, combined with 3,000 g of water, and agitated for 30 minutes. The liquid was filtered and dehydrated using a pressure filter holder. The dehydrated mass was similarly washed and dehydrated again. The dehydrated mass was dried in a hot gas fluidized bed dryer at a temperature of 105° C. The dry product was disintegrated by a jet mill, obtaining a free-flowing particle powder.

Particles were observed under an electron microscope, finding that surfaces of spherical particles were covered with particulates of about 100 nm, that is, silicone elastomer spherical particles were coated with polyorganosilsesquioxane. The filtrate resulting from the dehydrating step was colorless and clear, indicating that titanium oxide nano-particles were absent in the filtrate and all contained in the polyorganosilsesquioxane. Further, particles were observed under a transmission electron microscope coupled with an energy dispersive x-ray spectrometer to carry out titanium atom mapping, finding titanium atoms throughout the particle. It was thus judged that titanium oxide nano-particles were contained in the polyorganosilsesquioxane. Particles were dispersed in water with the aid of a surfactant for measuring a particle size distribution by instrument Multisizer 3 (Beckman Coulter), finding a volume average particle size of 5 μm.

Separately, methylvinylpolysiloxane of formula (1) having a viscosity of 580 $mm^2/s$, methylhydrogenpolysiloxane of formula (2) having a viscosity of 30 $mm^2/s$, and a toluene solution of chloroplatinic acid-olefin complex (platinum content 0.5 wt %) were mixed in the same proportion as above. The mixture was poured into an aluminum dish to a height of 10 mm. The mixture was allowed to stand at 25° C. for 24 hours, after which it was heated in a thermostat chamber at 50° C. for 1 hour, yielding a tack-free silicone elastomer. The silicone elastomer had a hardness of 29 as measured by a Durometer A hardness meter.

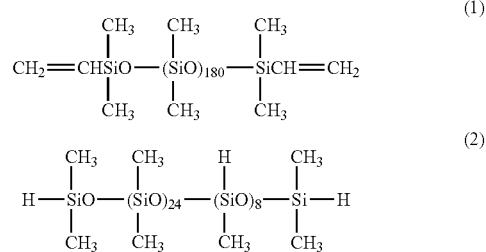

Example 2

Iron Oxide-Laden Silicone Resin-Coated Silicone Elastomer Composite Particles

As in Example 1, a water dispersion of silicone elastomer spherical particles was prepared. 867 g of the water dispersion of silicone elastomer spherical particles was transferred into a 3-liter glass flask equipped with an agitator having an anchor shaped impeller, to which were added 33 g of a water dispersion of iron oxide nano-particles (trade name, JC-FH04, by JFE Chemical Co., Ltd., average particle size 70 nm) (to give 7.3 parts of iron oxide per 100 parts of silicone elastomer spherical particles), 10 g of 30 wt % dodecyltrimethylammonium chloride aqueous solution, 1,975 g of water and 57 g of 28 wt % ammonia water. At this point, the liquid was at pH 11.2. After it was conditioned at 5-10° C., 58 g of methyltrimethoxysilane (to give 6.3 parts of polyorganosilsesquioxane per 100 parts of silicone elastomer spherical particles after hydrolytic condensation reaction) was added dropwise over 20 minutes. While the liquid was maintained at a temperature of 5-10° C., agitation was continued for a further 1 hour. The liquid was then heated at 55-60° C. At the temperature, agitation was continued for 1 hour for bringing hydrolytic condensation reaction of methyltrimethoxysilane to completion.

After the hydrolytic condensation reaction, the liquid was filtered and dehydrated using a pressure filter holder with a filter paper (trade name, quantitative filter paper No. 5C, Advantec Toyo Kaisha, Ltd., retaining particle size 1 μm). The dehydrated mass was transferred into a 5-liter glass flask equipped with an agitator having an anchor shaped impeller, combined with 3,000 g of water, and agitated for 30 minutes. The liquid was filtered and dehydrated using a pressure filter holder. The dehydrated mass was similarly washed and dehydrated again. The dehydrated mass was dried in a hot gas fluidized bed dryer at a temperature of 105° C. The dry product was disintegrated by a jet mill, obtaining a free-flowing particle powder.

Particles were observed under an electron microscope, finding that surfaces of spherical particles were covered with particulates of about 100 nm, that is, silicone elastomer spherical particles were coated with polyorganosilsesquioxane. The filtrate resulting from the dehydrating step was colorless and clear, indicating that iron oxide nano-particles were absent in the filtrate and all contained in the polyorganosilsesquioxane. Particles were dispersed in water with the aid of a surfactant for measuring a particle size distribution by instrument Multisizer 3 (Beckman Coulter), finding a volume average particle size of 5 μm.

Example 3

Zinc Oxide-Laden Silicone Resin-Coated Silicone Elastomer Composite Particles

As in Example 1, a water dispersion of silicone elastomer spherical particles was prepared. 867 g of the water dispersion of silicone elastomer spherical particles was transferred into a 3-liter glass flask equipped with an agitator having an anchor shaped impeller, to which were added 51 g of a water dispersion of zinc oxide nano-particles (trade name, ZW-143, by Sumitomo Osaka Cement Co., Ltd., zinc oxide concentration 30 wt %, average particle size 20 nm) (to give 3.4 parts of zinc oxide per 100 parts of silicone elastomer spherical particles), 1,967 g of water and 57 g of 28 wt % ammonia water. At this point, the liquid was at pH 11.3. After it was conditioned at 5-10° C., a mixture of 58 g of methyltrimethoxysilane and 2 g of γ-aminopropyltrimethoxysilane (to give 6.4 parts of polyorganosilsesquioxane per 100 parts of silicone elastomer spherical particles after hydrolytic condensation reaction) was added dropwise over 20 minutes. While the liquid was maintained at a temperature of 5-10° C., agitation was continued for a further 1 hour. The liquid was then heated at 55-60° C. At the temperature, agitation was continued for 1 hour for bringing hydrolytic condensation reaction between methyltrimethoxysilane and γ-aminopropyltrimethoxysilane to completion.

After the hydrolytic condensation reaction, the liquid was filtered and dehydrated using a pressure filter holder with a filter paper (trade name, quantitative filter paper No. 5C, Advantec Toyo Kaisha, Ltd., retaining particle size 1 μm). The dehydrated mass was transferred into a 5-liter glass flask equipped with an agitator having an anchor shaped impeller, combined with 3,000 g of water, and agitated for 30 minutes. The liquid was filtered and dehydrated using a pressure filter holder. The dehydrated mass was similarly washed and dehydrated again. The dehydrated mass was dried in a hot gas fluidized bed dryer at a temperature of 105° C. The dry product was disintegrated by a jet mill, obtaining a free-flowing particle powder.

Particles were observed under an electron microscope, finding that surfaces of spherical particles were covered with particulates of about 100 nm, that is, silicone elastomer spherical particles were coated with polyorganosilsesquioxane. The filtrate resulting from the dehydrating step was colorless and clear, indicating that zinc oxide nano-particles were absent in the filtrate and all contained in the polyorganosilsesquioxane. Particles were dispersed in water with the aid of a surfactant for measuring a particle size distribution by instrument Multisizer 3 (Beckman Coulter), finding a volume average particle size of 5 μm.

Example 4

Silver-Laden Silicone Resin-Coated Silicone Elastomer Composite Particles

As in Example 1, a water dispersion of silicone elastomer spherical particles was prepared. 867 g of the water dispersion of silicone elastomer spherical particles was transferred into a 3-liter glass flask equipped with an agitator having an anchor shaped impeller, to which were added 600 g of a water dispersion of silver nano-particles (trade name, Silver Colloid Solution, by Johzen Co., Ltd., silver concentration 0.0075 wt %, average particle size 10 nm) (to give 0.01 part of silver per 100 parts of silicone elastomer spherical particles), 1,418 g of water and 57 g of 28 wt % ammonia water. At this point, the liquid was at pH 11.5. After it was conditioned at 5-10° C., a mixture of 57 g of methyltrimethoxysilane and 1 g of γ-aminopropyltrimethoxysilane (to give 6.4 parts of polyorganosilsesquioxane per 100 parts of silicone elastomer spherical particles after hydrolytic condensation reaction) was added dropwise over 20 minutes. While the liquid was maintained at a temperature of 5-10° C., agitation was continued for a further 1 hour. The liquid was then heated at 55-60° C. At the temperature, agitation was continued for 1 hour for bringing hydrolytic condensation reaction between methyltrimethoxysilane and γ-aminopropyltrimethoxysilane to completion.

After the hydrolytic condensation reaction, the liquid was filtered and dehydrated using a pressure filter holder with a filter paper (trade name, quantitative filter paper No. 5C, Advantec Toyo Kaisha, Ltd., retaining particle size 1 μm). The dehydrated mass was transferred into a 5-liter glass flask equipped with an agitator having an anchor shaped impeller, combined with 3,000 g of water, and agitated for 30 minutes. The liquid was filtered and dehydrated using a pressure filter holder. The dehydrated mass was similarly washed and dehydrated again. The dehydrated mass was dried in a hot gas fluidized bed dryer at a temperature of 105° C. The dry product was disintegrated by a jet mill, obtaining a free-flowing particle powder.

Particles were observed under an electron microscope, finding that surfaces of spherical particles were covered with particulates of about 100 nm, that is, silicone elastomer spherical particles were coated with polyorganosilsesquioxane. The filtrate resulting from the dehydrating step was colorless and clear, indicating that silver nano-particles were absent in the filtrate and all contained in the polyorganosilsesquioxane. Particles were dispersed in water with the aid of a surfactant for measuring a particle size distribution by instrument Multisizer 3 (Beckman Coulter), finding a volume average particle size of 5 μm.

Comparative Example 1

Silicone Resin-Coated Silicone Elastomer Composite Particles

As in Example 1, a water dispersion of silicone elastomer spherical particles was prepared. 867 g of the water dispersion of silicone elastomer spherical particles was transferred into a 3-liter glass flask equipped with an agitator having an anchor shaped impeller, to which were added 2,017 g of water and 57 g of 28 wt % ammonia water. At this point, the liquid was at pH 11.2. After it was conditioned at 5-10° C., 59 g of methyltrimethoxysilane (to give 6.5 parts of polyorganosilsesquioxane per 100 parts of silicone elastomer spherical particles after hydrolytic condensation reaction) was added dropwise over 20 minutes. While the liquid was maintained at a temperature of 5-10° C., agitation was continued for a further 1 hour. The liquid was then heated at 55-60° C. At the temperature, agitation was continued for 1 hour for bringing hydrolytic condensation reaction of methyltrimethoxysilane to completion.

After the hydrolytic condensation reaction, the liquid was filtered and dehydrated using a pressure filter holder with a filter paper (trade name, quantitative filter paper No. 5C, Advantec Toyo Kaisha, Ltd., retaining particle size 1 μm). The dehydrated mass was transferred into a 5-liter glass flask equipped with an agitator having an anchor shaped impeller, combined with 3,000 g of water, and agitated for 30 minutes. The liquid was filtered and dehydrated using a pressure filter holder. The dehydrated mass was similarly washed and dehydrated again. The dehydrated mass was dried in a hot gas fluidized bed dryer at a temperature of 105° C. The dry product was disintegrated by a jet mill, obtaining a free-flowing particle powder.

Particles were observed under an electron microscope, finding that surfaces of spherical particles were covered with particulates of about 100 nm, that is, silicone elastomer spherical particles were coated with polyorganosilsesquioxane. Particles were dispersed in water with the aid of a surfactant for measuring a particle size distribution by instrument Multisizer 3 (Beckman Coulter), finding a volume average particle size of 5 μm.

Example 5 and Comparative Examples 2, 3

Sun Care Milk

A sun care milk was prepared by using particles obtained in Example 1 or Comparative Example 1 and suitable ingredients, combining them in accordance with the formulation (wt %) shown in Table 1, and processing by the following procedure. The sun care milk thus obtained was evaluated by the following tests.

TABLE 1

| No. | Formulation (wt %) | Example 5 | Comparative Example 2 | Comparative Example 3 |
|---|---|---|---|---|
| 1 | Titanium oxide-laden silicone resin-coated silicone elastomer composite particles (Example 1) | 2.5 | — | — |
| 2 | Silicone resin-coated silicone elastomer composite particles (Comparative Example 1) | — | 2.5 | — |
| 3 | Crosslinkable polyether-modified silicone[1] | 3.0 | 3.0 | 3.0 |
| 4 | Crosslinkable dimethylpolysiloxane[2] | 2.0 | 2.0 | 2.0 |
| 5 | Polyether-modified branched silicone[3] | 1.0 | 1.0 | 1.0 |
| 6 | Decamethylcyclopentasiloxane | 5.0 | 5.0 | 5.0 |
| 7 | Isononyl isononanoate | 4.0 | 4.0 | 4.0 |
| 8 | Dimethylpolysiloxane (6 mm$^2$/s) | 2.5 | 2.5 | 5.0 |
| 9 | Dispersion of titanium oxide nano-particles in silicone[4] | 25.0 | 25.0 | 25.0 |
| 10 | Dispersion of zinc oxide nano-particles in silicone[5] | 35.0 | 35.0 | 35.0 |
| 11 | Dipropylene glycol | 2.0 | 2.0 | 2.0 |
| 12 | Sodium citrate | 0.2 | 0.2 | 0.2 |
| 13 | Sodium chloride | 1.0 | 1.0 | 1.0 |
| 14 | Water | 16.8 | 16.8 | 16.8 |
|   | Total | 100.0 | 100.0 | 100.0 |

[1]Crosslinkable polyether-modified silicone: KSG-210 by Shin-Etsu Chemical Co., Ltd.
[2]Crosslinkable dimethylpolysiloxane: KSG-15 by Shin-Etsu Chemical Co., Ltd.
[3]Polyether-modified branched silicone: KF-6028 by Shin-Etsu Chemical Co., Ltd.
[4]Dispersion of titanium oxide nano-particles in silicone: SPD-T5 by Shin-Etsu Chemical Co., Ltd.
[5]Dispersion of zinc oxide nano-particles in silicone: SPD-Z5 by Shin-Etsu Chemical Co., Ltd.

Preparation of Sun Care Milk

In a beaker, ingredients 1 to 8 were agitated and mixed. To the mixture was added a solution which was separately prepared by dissolving ingredients 11 to 13 in ingredient 14. Agitation and mixing was continued to form a base emulsion. To this were added ingredients 9 and 10. Agitation and mixing was continued to form a sun care milk.

Evaluation of UV Screening Effect

The sun care milk was evaluated for UV screening effect. Sun Protection Factor (SPF) was evaluated according to the COLIPA International Sun Protection Factor Test Method (to which the Japan Cosmetic Industry Association (JCIA) agreed) except that the panel consisted of two persons. Protection grade of WA (PA) was evaluated by the PA Test Method of JCIA except that the panel consisted of two persons. The results are shown in Table 2.

TABLE 2

| UV screening effect | | |
|---|---|---|
| | SPF | PA |
| Example 5 | 51.3 | 7.9 |
| Comparative Example 2 | 46.6 | 7.8 |
| Comparative Example 3 | 51.4 | 7.9 |

* SPF and PA values each are an average of measurements of two persons.

Use Test

The sun care milk was also evaluated by a panel of 20 professional women. A cosmetic sample was applied to the skin, examined for "spread", "adhesion" (uniform application), "smoothness", and "softness", and rated according to the rating point scale of Table 3. An average point was calculated for each factor, and the sample was evaluated according to the criterion shown below. The results are shown in Table 4.

TABLE 3

| Rating point table | | | | |
|---|---|---|---|---|
| Point | Spread | Adhesion | Smoothness | Softness |
| 5 | excellent | excellent | excellent | excellent |
| 4 | good | good | good | good |
| 3 | moderate | moderate | moderate | moderate |
| 2 | poor | poor | poor | poor |
| 1 | bad | bad | bad | bad |

Evaluation Criterion

⊚: 4.5≤average point
○: 3.5≤average point<4.5
Δ: 2.5≤average point<3.5
x: 1.5≤average point<2.5
xx: average point<1.5

TABLE 4

| | Example | Comparative Example | |
|---|---|---|---|
| | 5 | 2 | 3 |
| Spread | ⊚ | ⊚ | Δ |
| Adhesion | ⊚ | ⊚ | Δ |
| Smoothness | ⊚ | ⊚ | Δ |
| Softness | ⊚ | ⊚ | Δ |

It is seen from the results of Table 2 that Comparative Example 2 is inferior in UV screening effect to Comparative Example 3. It is seen from the results of Table 3 that Comparative Example 2 is superior in usability to Comparative Example 3. The compounding of silicone composite particles improves usability at the sacrifice of UV screening effect. In contrast, Example 5 having the inventive silicone composite particles compounded therein imparts a feeling-on-use inherent to silicone composite particles and improves usability without detracting from the UV screening effect. Similarly, when an antiperspirant aerosol was prepared by compounding 5.0 wt % of the silver-laden silicone resin-coated silicone elastomer composite particles of Example 4, it was endowed with a bactericidal effect and a feeling-on-use inherent to silicone composite particles.

Using the particles of Examples, various cosmetic compositions were prepared in a conventional manner.

Example 6

| Powder foundation | | |
|---|---|---|
| | Ingredients | wt % |
| 1 | Liquid paraffin | 2.0 |
| 2 | Squalane | 2.0 |
| 3 | Dimethylpolysiloxane (20 mm$^2$/s) | 3.0 |
| 4 | Polyethylene | 1.5 |
| 5 | Methylhydrogenpolysiloxane-treated mica | 40.0 |
| 6 | Barium sulfate | 10.0 |
| 7 | Metal soap-treated titanium oxide | 9.0 |
| 8 | Titanium oxide-laden silicone resin-coated silicone elastomer composite particles of Example 1 | 3.0 |
| 9 | Zinc oxide-laden silicone resin-coated silicone elastomer composite particles of Example 3 | 3.0 |
| 10 | Methylhydrogenpolysiloxane-treated talc | 26.5 |
| 11 | Triethoxysilylethylpolydimethylsiloxyethylhexyl dimethicone-treated iron oxide pigment | appropriate |
| | Total | 100.0 |

Note that triethoxysilylethylpolydimethylsiloxyethylhexyl dimethicone is KF-9909 by Shin-Etsu Chemical Co., Ltd.

Preparation Procedure

A: Ingredients 4 to 11 were admitted in a Henschel mixer where they were agitated and mixed.

B: Ingredients 1 to 3 were heat dissolved and added to A, followed by agitation and mixing.

C: The resulting mixture was ground by a hammer mill and press molded in a given aluminum pan to form a powder foundation.

The powder foundation thus obtained had a fine texture and was lightly spreadable, free of a greasy or oily feel, and cosmetically long lasting.

Example 7

| O/W type cream | | |
|---|---|---|
| | Ingredients | wt % |
| 1 | Crosslinkable dimethylpolysiloxane* | 10.0 |
| 2 | Glyceryl trioctanoate | 5.0 |
| 3 | Titanium oxide-laden silicone resin-coated silicone elastomer composite particles of Example 1 | 1.0 |
| 4 | Dipropylene glycol | 7.0 |
| 5 | Glycerol | 5.0 |
| 6 | Methyl cellulose (2 wt % aqueous solution)** | 7.0 |
| 7 | Polyacrylamide emulsifier*** | 2.0 |

-continued

| O/W type cream | | |
|---|---|---|
| | Ingredients | wt % |
| 8 | Preservative | appropriate |
| 9 | Perfume | appropriate |
| 10 | Water | balance |
| | Total | 100.0 |

*Crosslinkable dimethylpolysiloxane: KSG-16 by Shin-Etsu Chemical Co., Ltd.
**Methyl cellulose: Metrose SM-4000 by Shin-Etsu Chemical Co., Ltd.
***Polyacrylamide emulsifier; Sepigel 305 by SEPIC Preparation Procedure A: Ingredients 4 to 10 were mixed.
B: Ingredients 1 to 3 were mixed and added to A, followed by agitation and emulsification.

The O/W type cream thus obtained had a fine texture and was lightly spreadable and free of a greasy or oily feel. It showed no changes with temperature and time and remained stable.

Example 8

| W/O type cream | | |
|---|---|---|
| | Ingredients | wt % |
| 1 | Dimethylpolysiloxane (6 mm$^2$/s) | 6.0 |
| 2 | Methylphenylpolysiloxane | 4.0 |
| 3 | Squalane | 5.0 |
| 4 | Neopentyl glycol dioctanoate | 3.0 |
| 5 | Polyether-modified silicone* | 3.0 |
| 6 | Titanium oxide-laden silicone resin-coated silicone elastomer composite particles of Example 1 | 2.0 |
| 7 | Glycerol | 10.0 |
| 8 | Preservative | appropriate |
| 9 | Perfume | appropriate |
| 10 | Water | balance |
| | Total | 100.0 |

*Polyether-modified silicone: KF-6012 by Shin-Etsu Chemical Co., Ltd.

Preparation Procedure

A: Ingredients 1 to 5 were mixed, to which ingredient 6 was added. The contents were mixed until uniform.
B: Ingredients 7, 8 and 10 were mixed and dissolved.
C: While agitation was continued, B was slowly added to A to form an emulsion. Ingredient 9 was added to the emulsion to form a cream.

The W/O type cream thus obtained had a fine texture and was lightly spreadable and free of a greasy or oily feel. It showed no changes with temperature and time and remained stable.

Example 9

| W/O type cream | | |
|---|---|---|
| | Ingredients | wt % |
| 1 | Alkyl-modified crosslinkable polyether-modified silicone* | 6.0 |
| 2 | Liquid paraffin | 13.5 |
| 3 | Macadamia nut oil | 5.0 |
| 4 | Alkyl/polyether co-modified silicone** | 0.5 |
| 5 | Hybrid silicone composite powder*** | 3.0 |

-continued

| W/O type cream | | |
|---|---|---|
| | Ingredients | wt % |
| 6 | Titanium oxide-laden silicone resin-coated silicone elastomer composite particles of Example 1 | 2.0 |
| 7 | Sodium citrate | 0.2 |
| 8 | Propylene glycol | 8.0 |
| 9 | Glycerol | 3.0 |
| 10 | Preservative | appropriate |
| 11 | Perfume | appropriate |
| 12 | Water | balance |
| | Total | 100.0 |

*Alkyl-modified crosslinkable polyether-modified silicone: KSG-310 by Shin-Etsu Chemical Co., Ltd.
**Alkyl/polyether co-modified silicone: KF-6038 by Shin-Etsu Chemical Co., Ltd.
***Hybrid silicone composite powder: KSP-100 by Shin-Etsu Chemical Co., Ltd.

Preparation Procedure

A: Ingredients 1 to 6 were mixed.
B: Ingredients 7 to 12 were mixed and dissolved. This was added to A and agitated for emulsyfication.

The W/O type cream thus obtained had a fine texture and was lightly spreadable and free of a greasy or oily feel. It showed no changes with temperature and time and remained stable.

Example 10

| W/O type cream | | |
|---|---|---|
| | Ingredients | wt % |
| 1 | Decamethylcyclopentasiloxane | 20.5 |
| 2 | Dimethylpolysiloxane (6 mm$^2$/s) | 4.0 |
| 3 | Polyether-modified silicone* | 5.0 |
| 4 | POE (5) octyl dodecyl ether | 1.0 |
| 5 | Monostearic acid polyoxyethylene sorbitan (20 E.O.) | 0.5 |
| 6 | Titanium oxide-laden silicone resin-coated silicone elastomer composite particles of Example 1 | 5.0 |
| 7 | Liquid paraffin | 2.0 |
| 8 | Macadamia nut oil | 1.0 |
| 9 | *Scutellaria baicalensis* extract** | 1.0 |
| 10 | *Gentian* extract*** | 0.5 |
| 11 | Ethanol | 5.0 |
| 12 | 1,3-butylene glycol | 2.0 |
| 13 | Preservative | appropriate |
| 14 | Perfume | appropriate |
| 15 | Water | balance |
| | Total | 100.0 |

*Polyether-modified silicone: KF-6017 by Shin-Etsu Chemical Co., Ltd.
**Scutellaria baicalensis extract: extracted with 50% 1,3-butylene glycol in water
***Gentian extract: extracted with 20% ethanol in water Preparation Procedure A: Ingredients 1 to 8 were mixed and dispersed until uniform.
B: Ingredients 9 to 13 and 15 were mixed. The mixture was added to A, which was emulsified.
C: Ingredient 14 was added to B to form a cream.

The W/O type cream thus obtained had a fine texture and was lightly spreadable and free of a greasy feel. It adhered well to the skin and cosmetically lasted long. It showed no changes with temperature and time and remained stable.

Example 11

| Eye liner | | |
|---|---|---|
| | Ingredients | wt % |
| 1 | Decamethylcyclopentasiloxane | 39.0 |
| 2 | Polyether-modified silicone* | 3.0 |
| 3 | Organic silicone resin** | 15.0 |
| 4 | Dioctadecyldimethylammonium salt-modified montmorillonite | 3.0 |
| 5 | Methylhydrogenpolysiloxane-treated black iron oxide | 8.0 |
| 6 | Iron oxide-laden silicone resin-coated silicone elastomer composite particles of Example 2 | 2.0 |
| 7 | 1,3-butylene glycol | 5.0 |
| 8 | Sodium dehydroacetate | appropriate |
| 9 | Preservative | appropriate |
| 10 | Water | balance |
| | Total | 100.0 |

*Polyether-modified silicone: KF-6017 by Shin-Etsu Chemical Co., Ltd.
**Organic silicone resin: KF-7312J by Shin-Etsu Chemical Co., Ltd.

Preparation Procedure
 A: Ingredients 1 to 4 were mixed. Ingredients 5 and 6 were added. The contents were mixed and dispersed until uniform.
 B: Ingredients 7 to 10 were mixed.
 C: B was slowly added to A, which was emulsified to form an eye liner.

The eye liner thus obtained was lightly spreadable and easy to draw. It had a refreshing, light, non-greasy feeling on use. It showed no changes with temperature and time. It had superior usability, stability, and resistance to water and perspiration, and cosmetically lasted long.

Example 12

| Foundation | | |
|---|---|---|
| | Ingredients | wt % |
| 1 | Decamethylcyclopentasiloxane | 45.0 |
| 2 | Dimethylpolysiloxane (6 mm$^2$/s) | 15.0 |
| 3 | Polyether-modified silicone* | 3.5 |
| 4 | Octadecyldimethylbenzylammonium salt-modified montmorillonite | 1.5 |
| 5 | Zinc oxide-laden silicone resin-coated silicone elastomer composite particles of Example 3 | 4.5 |
| 6 | Triethoxysilylethylpolydimethylsiloxyethylhexyl dimethicone**-treated iron oxide | 2.5 |
| 7 | Triethoxysilylethylpolydimethylsiloxyethylhexyl dimethicone**-treated titanium oxide | 7.5 |
| 8 | Dipropylene glycol | 5.0 |
| 9 | Methyl p-hydroxybenzoate | 0.3 |
| 10 | Perfume | appropriate |
| 11 | Water | balance |
| | Total | 100.0 |

*Polyether-modified silicone: KF-6017 by Shin-Etsu Chemical Co., Ltd.
**Triethoxysilylethylpolydimethylsiloxyethylhexyl dimethicone: KF-9909 by Shin-Etsu Chemical Co., Ltd.

Preparation Procedure
 A: Ingredients 1 to 4 were mixed, to which ingredients 5 to 7 were added. The contents were mixed until uniform.
 B: Ingredients 8, 9 and 11 were dissolved.
 C: While agitation was continued, B was slowly added to A to form an emulsion. Ingredient 10 was added thereto to form a foundation.

The foundation thus obtained had a fine texture and was lightly spreadable and free of a greasy or oily feel. It cosmetically lasted long. It showed no changes with temperature and time and remained stable.

Example 13

| Eye shadow | | |
|---|---|---|
| | Ingredients | wt % |
| 1 | Decamethylcyclopentasiloxane | 15.0 |
| 2 | Dimethylpolysiloxane (6 mm$^2$/s) | 10.0 |
| 3 | Polyether-modified branched silicone* | 2.0 |
| 4 | PEG (10) lauryl ether | 0.5 |
| 5 | Iron oxide-laden silicone resin-coated silicone elastomer composite particles of Example 2 | 6.0 |
| 6 | Methylhydrogenpolysiloxane-treated inorganic pigment | appropriate |
| 7 | Sodium chloride | 2.0 |
| 8 | Propylene glycol | 8.0 |
| 9 | Preservative | appropriate |
| 10 | Perfume | appropriate |
| 11 | Water | balance |
| | Total | 100.0 |

*Polyether-modified branched silicone: KF-6028 by Shin-Etsu Chemical Co., Ltd.

Preparation Procedure
 A: Ingredients 1 to 4 were mixed, to which ingredients 5 and 6 were added. The contents were mixed and dispersed until uniform.
 B: Ingredients 7 to 9 were homogeneously dissolved in ingredient 11.
 C: While agitation was continued, B was slowly added to A to form an emulsion. Ingredient 10 was added thereto to form an eye shadow.

The eye shadow thus obtained was lightly spreadable and free of oily or powdery feel, and had a good feeling on use. It had water resistance, water repellency, perspiration resistance, and long-lasting quality, and cosmetically little deteriorated. It showed no changes with temperature and time and remained stable.

Example 14

| Lipstick | | |
|---|---|---|
| | Ingredients | wt % |
| 1 | Candelilla wax | 8.0 |
| 2 | Polyethylene wax | 8.0 |
| 3 | Long chain alkyl-containing acrylic silicone resin* | 12.0 |
| 4 | Methylphenylpolysiloxane** | 3.0 |
| 5 | Isotridecyl isononanoate | 20.0 |
| 6 | Glyceryl isostearate | 16.0 |
| 7 | Polyglyceryl triisostearate | 28.5 |
| 8 | Titanium oxide-laden silicone resin-coated silicone elastomer composite particles of Example 1 | 1.5 |
| 9 | Organic pigment | appropriate |
| 10 | Perfume | appropriate |
| | Total | 100.0 |

*Long chain alkyl-containing acrylic silicone resin: KP-561P by Shin-Etsu Chemical Co., Ltd.
**Methylphenylpolysiloxane: KF-54 by Shin-Etsu Chemical Co., Ltd.

Preparation Procedure
- A: Ingredients 1 to 6 and part of ingredient 7 were heated, mixed and dissolved.
- B: Ingredients 8 and 9 and remainder of ingredient 7 were uniformly mixed. This was added to A and mixed until uniform.
- C: Ingredient 10 was added to B to form a lipstick.

The lipstick thus obtained was lightly spreadable and free of oily or powdery feel. It had water resistance, water repellency, long-lasting quality, and stability.

Example 15

| Eye liner | | |
|---|---|---|
| Ingredients | | wt % |
| 1 | Decamethylcyclopentasiloxane | 6.0 |
| 2 | Dimethylpolysiloxane (6 mm$^2$/s) | 5.0 |
| 3 | Jojoba oil | 2.0 |
| 4 | Polyether-modified silicone* | 1.0 |
| 5 | Alkyl/polyether co-modified silicone** | 1.0 |
| 6 | Acrylic silicone resin*** | 15.0 |
| 7 | Iron oxide-laden silicone resin-coated silicone elastomer composite particles of Example 2 | 2.0 |
| 8 | Methylhydrogenpolysiloxane-treated black iron oxide | 18.0 |
| 9 | Ethanol | 5.0 |
| 10 | Preservative | appropriate |
| 11 | Water | balance |
| | Total | 100.0 |

*Polyether-modified silicone: KF-6017 by Shin-Etsu Chemical Co., Ltd.
**Alkyl/polyether co-modified silicone: KF-6038 by Shin-Etsu Chemical Co., Ltd.
***Acrylic silicone resin: KP-545 by Shin-Etsu Chemical Co., Ltd.

Preparation Procedure
- A: Ingredients 1 to 6 were agitated and mixed, to which ingredients 7 and 8 were added. The contents were dispersed until uniform.
- B: Ingredients 9 to 11 were agitated and dissolved.
- C: With agitation, B was slowly added to A, which was emulsified to form an eye liner.

The eye liner thus obtained was lightly spreadable and free of an oily or powdery feel. It had water resistance, water repellency, perspiration resistance, and long-lasting quality. It was unlikely to cosmetically deteriorate. It showed no changes with temperature and time, and remained stable.

Example 16

| Liquid emulsified foundation | | |
|---|---|---|
| Ingredients | | wt % |
| 1 | Dimethylpolysiloxane (6 mm$^2$/s) | 4.5 |
| 2 | Decamethylcyclopentasiloxane | 15.0 |
| 3 | Squalane | 4.0 |
| 4 | Neopentyl glycol dioctanoate | 3.0 |
| 5 | Myristic acid isostearic acid diglyceride | 2.0 |
| 6 | α-monoisostearyl glyceryl ether | 1.0 |
| 7 | Polyether-modified silicone* | 1.0 |
| 8 | Alkyl/polyether co-modified silicone** | 0.5 |
| 9 | Aluminum distearate | 0.2 |
| 10 | Titanium oxide-laden silicone resin-coated silicone elastomer composite particles of Example 1 | 4.0 |
| 11 | Zinc oxide-laden silicone resin-coated silicone elastomer composite particles of Example 3 | 3.0 |
| 12 | Methylhydrogenpolysiloxane-treated iron oxide pigment | appropriate |
| 13 | Glycerol | 3.0 |
| 14 | Preservative | appropriate |
| 15 | Perfume | appropriate |
| 16 | Water | balance |
| | Total | 100.0 |

*Polyether-modified silicone: KF-6017 by Shin-Etsu Chemical Co., Ltd.
**Alkyl/polyether co-modified silicone: KF-6038 by Shin-Etsu Chemical Co., Ltd.

Preparation Procedure
- A: Ingredients 1 to 9 were heated and mixed, to which ingredients 10 to 12 were added. The contents were mixed until uniform.
- B: Ingredients 13 and 14 were heat dissolved in ingredient 16.
- C: With agitation, B was slowly added to A to form an emulsion. This was cooled, ingredient 15 was added thereto to form a liquid emulsified foundation.

The liquid emulsified foundation thus obtained had a low viscosity, fine texture, light spreadability, non-greasy or non-oily feel, skin contour regulating effect, and long-lasting cosmetic quality. It showed no changes with temperature and time and remained stable.

Example 17

| Liquid foundation | | |
|---|---|---|
| Ingredients | | wt % |
| 1 | Decamethylcyclopentasiloxane | 16.0 |
| 2 | Dimethylpolysiloxane (6 mm$^2$/s) | 8.0 |
| 3 | Octyl p-methoxysuccinate | 3.0 |
| 4 | 12-hydroxystearic acid | 1.0 |
| 5 | Fluorine-modified silicone* | 15.0 |
| 6 | Fluoroalkyl/polyether co-modified silicone** | 5.0 |
| 7 | Spherical powder polymethylsilsesquioxane*** | 1.0 |
| 8 | Titanium oxide-laden silicone resin-coated silicone elastomer composite particles of Example 1 | 3.0 |
| 9 | Zinc oxide-laden silicone resin-coated silicone elastomer composite particles of Example 3 | 3.0 |
| 10 | Methylhydrogenpolysiloxane-treated iron oxide pigment | appropriate |
| 11 | Ethanol | 15.0 |
| 12 | Glycerol | 3.0 |
| 13 | Magnesium sulfate | 1.0 |
| 14 | Preservative | appropriate |
| 15 | Perfume | appropriate |
| 16 | Water | balance |
| | Total | 100.0 |

*Fluorine-modified silicone: FL-50 by Shin-Etsu Chemical Co., Ltd.
**Fluoroalkyl/polyether co-modified silicone: FPD-4694 by Shin-Etsu Chemical Co., Ltd.
***Spherical powder polymethylsilsesquioxane: KMP-590 by Shin-Etsu Chemical Co., Ltd.

Preparation Procedure
- A: Ingredients 7 to 10 were mixed until uniform.
- B: Ingredients 1 to 6 were heat mixed at 70° C., to which A was added. The contents were mixed and dispersed until uniform.
- C: Ingredients 11 to 14 and 16 were heated at 40° C., slowly added to B to form an emulsion. After this was cooled, ingredient 15 was added thereto to form a liquid foundation.

The liquid foundation thus obtained had a non-greasy feel and light spreadability, showed no changes with temperature and time, and remained highly stable.

Example 18

| Eye liner | | |
|---|---|---|
| | Ingredients | wt % |
| 1 | Decamethylcyclopentasiloxane | 22.0 |
| 2 | Dimethylpolysiloxane (6 mm$^2$/s) | 5.0 |
| 3 | Methylhydrogenpolysiloxane-treated black iron oxide | 20.0 |
| 4 | Iron oxide-laden silicone resin-coated silicone elastomer composite particles of Example 2 | 1.0 |
| 5 | Organic silicone resin* | 10.0 |
| 6 | Vitamin E acetate | 0.2 |
| 7 | Jojoba oil | 2.0 |
| 8 | Bentonite | 3.0 |
| 9 | Polyether-modified silicone** | 2.0 |
| 10 | Ethanol | 3.0 |
| 11 | 1,3-butylene glycol | 5.0 |
| 12 | Preservative | appropriate |
| 13 | Water | balance |
| | Total | 100.0 |

*Organic silicone resin: KF-7312J by Shin-Etsu Chemical Co., Ltd.
**Polyether-modified silicone: KF-6017 by Shin-Etsu Chemical Co., Ltd.

Preparation Procedure
  A: Ingredients 1, 2, 5 to 9 were mixed, to which ingredients 3 and 4 were added. The contents were dispersed until uniform.
  B: Ingredients 10 to 13 were mixed.
  C: B was slowly added to A, which was emulsified to form an eye liner.

The eye liner thus obtained was lightly spreadable and easy to draw. It had a refreshing, light, non-greasy feeling on use. It had water resistance, perspiration resistance, and very long-lasting quality. It showed no changes with temperature and time.

Example 19

| Foundation | | |
|---|---|---|
| | Ingredients | wt % |
| 1 | Decamethylcyclopentasiloxane | 27.0 |
| 2 | Methylphenylpolysiloxane | 3.0 |
| 3 | Glyceryl trioctanoate | 10.0 |
| 4 | Polyether-modified silicone* | 4.0 |
| 5 | Monoisostearic acid polyglyceryl | 3.0 |
| 6 | Zinc oxide-laden silicone resin-coated silicone elastomer composite particles of Example 3 | 4.0 |
| 7 | Aluminum stearate-treated titanium oxide | 6.0 |
| 8 | Methylhydrogenpolysiloxane-treated iron oxide pigment | appropriate |
| 9 | 1,3-butylene glycol | 7.0 |
| 10 | Sodium chloride | 0.5 |
| 11 | Preservative | appropriate |
| 12 | Perfume | appropriate |
| 13 | Water | balance |
| | Total | 100.0 |

*Polyether-modified silicone: KF-6017 by Shin-Etsu Chemical Co., Ltd.

Preparation Procedure
  A: Ingredients 1 to 5 were mixed and dissolved, in which ingredients 6 to 8 were dispersed until uniform.
  B: Ingredients 9 to 11 and 13 were mixed, which was added to A to form an emulsion.
  C: Ingredient 12 was added to B to form a foundation.

The foundation thus obtained had a non-greasy feel, light spreadability, tight adhesion, and very long lasting quality. It showed no changes with temperature and time, and remained stable.

Example 20

| W/O type antiperspirant | | |
|---|---|---|
| | Ingredients | wt % |
| 1 | Crosslinkable polyether-modified silicone* | 7.0 |
| 2 | Decamethylcyclopentasiloxane | 10.0 |
| 3 | Glyceryl trioctanoate | 7.0 |
| 4 | Dipropylene glycol | 5.0 |
| 5 | Sodium citrate | 0.2 |
| 6 | Aluminum zirconium tetrachlorohydrate | 18.0 |
| 7 | Silver-laden silicone resin-coated silicone elastomer composite particles of Example 4 | 5.0 |
| 8 | Phenyl-modified hybrid silicone composite powder** | 2.0 |
| 9 | Perfume | appropriate |
| 10 | Water | 45.8 |
| | Total | 100.0 |

*Crosslinkable polyether-modified silicone: KSG-210 by Shin-Etsu Chemical Co., Ltd.
**Phenyl-modified hybrid silicone composite powder: KSP-300 by Shin-Etsu Chemical Co., Ltd.

Preparation Procedure
  A: Ingredients 1 to 3 were mixed.
  B: Ingredients 4 to 10 were mixed.
  C: B was added to A, which was mixed and emulsified.

The W/O type antiperspirant thus obtained was lightly spreadable and free of a greasy or oily feel. It showed no changes with temperature and time, and a very good usability and stability.

Example 21

| Roll-on type antiperspirant | | |
|---|---|---|
| | Ingredients | wt % |
| 1 | Crosslinkable polyether-modified silicone* | 20.0 |
| 2 | Dimethylpolysiloxane (6 mm$^2$/s) | 10.0 |
| 3 | Crosslinkable dimethylpolysiloxane** | 15.0 |
| 4 | Decamethylcyclopentasiloxane | 30.0 |
| 5 | Aluminum zirconium tetrachlorohydrate | 20.0 |
| 6 | Silver-laden silicone resin-coated silicone elastomer composite particles of Example 4 | 5.0 |
| 7 | Perfume | appropriate |
| | Total | 100.0 |

*Crosslinkable polyether-modified silicone: KSG-210 by Shin-Etsu Chemical Co., Ltd.
**Crosslinkable dimethylpolysiloxane: KSG-15 by Shin-Etsu Chemical Co., Ltd.

Preparation Procedure
  A: Ingredients 1 to 4 were mixed.
  B: Ingredients 5 to 7 were added to A. The contents were dispersed until uniform.

The roll-on type antiperspirant thus obtained was lightly spreadable and free of a greasy or oily feel. It showed no changes with temperature and time, and a very good usability and stability.

Example 22

Sunburn protection emulsion

| | Ingredients | wt % |
|---|---|---|
| 1 | Decamethylcyclopentasiloxane | 20.0 |
| 2 | Methylphenylpolysiloxane | 3.0 |
| 3 | Monoisostearic acid sorbitan | 1.0 |
| 4 | Polyether-modified silicone* | 0.5 |
| 5 | Trimethylsiloxysilicic acid** | 1.0 |
| 6 | Octyl p-methoxysuccinate | 4.0 |
| 7 | Zinc oxide-laden silicone resin-coated silicone elastomer composite particles of Example 3 | 2.0 |
| 8 | Aluminum stearate-treated titanium oxide nano-particles | 6.0 |
| 9 | Sorbitol | 2.0 |
| 10 | Sodium chloride | 2.0 |
| 11 | Preservative | appropriate |
| 12 | Perfume | appropriate |
| 13 | Water | balance |
| | Total | 100.0 |

*Polyether-modified silicone: KF-6015 by Shin-Etsu Chemical Co., Ltd.
**Trimethylsiloxysilicic acid: X-21-5250 by Shin-Etsu Chemical Co., Ltd.

Preparation Procedure

A: Ingredients 1 to 6 were heat mixed. Ingredients 7 and 8 were dispersed therein until uniform.

B: Ingredients 9 to 11 and 13 were heat mixed.

C: With agitation, B was slowly added to A to form an emulsion. This was cooled, to which ingredient 12 was added, obtaining a sunburn protection emulsion.

The sunburn protection emulsion thus obtained had a fine texture, and was lightly spreadable and free of a greasy feel. Due to a long lasting quality, it maintained a UV screening effect. It showed no changes with temperature and time, and remained highly stable.

Example 23

Sun-cut cream

| | Ingredients | wt % |
|---|---|---|
| 1 | Decamethylcyclopentasiloxane | 17.5 |
| 2 | Acrylic silicone resin* | 12.0 |
| 3 | Glyceryl trioctanoate | 5.0 |
| 4 | Octyl p-methoxysuccinate | 6.0 |
| 5 | Crosslinkable polyether-modified silicone** | 5.0 |
| 6 | Alkyl silicone/polyether co-modified silicone*** | 2.5 |
| 7 | Zinc oxide-laden silicone resin-coated silicone elastomer composite particles of Example 3 | 2.0 |
| 8 | Aluminum stearate-treated titanium oxide nano-particles | 15.0 |
| 9 | Sodium chloride | 0.5 |

Sun-cut cream

| | Ingredients | wt % |
|---|---|---|
| 10 | 1,3-butylene glycol | 2.0 |
| 11 | Preservative | appropriate |
| 12 | Perfume | appropriate |
| 13 | Water | balance |
| | Total | 100.0 |

*Acrylic silicone resin: KP-545 by Shin-Etsu Chemical Co., Ltd.
**Crosslinkable polyether-modified silicone: KSG-210 by Shin-Etsu Chemical Co., Ltd.
***Alkyl silicone/polyether co-modified silicone: KF-6038 by Shin-Etsu Chemical Co., Ltd.

Preparation Procedure

A: Ingredient 2 was added to part of ingredient 1 and mixed until uniform. Ingredient 8 was added thereto and dispersed in a bead mill.

B: Remainder of ingredient 1 and ingredients 3 to 7 were mixed until uniform.

C: Ingredients 9 to 11 were mixed and dissolved in ingredient 13.

D: C was added to B and emulsified. A was dispersed in this emulsion, to which ingredient 12 was added, obtaining a sun-cut cream.

The sun-cut cream thus obtained had a non-greasy feel, light spreadability, tight adhesion to the skin, skin contour regulating effect, and long lasting cosmetic quality. It remained stable against temperature changes and with the lapse of time.

Example 24

Nail enamel

| | Ingredients | wt % |
|---|---|---|
| 1 | Acrylic silicone resin* | 45.0 |
| 2 | Methyl trimethicone** | 5.0 |
| 3 | Nitrocellulose | 3.0 |
| 4 | Camphor | 0.5 |
| 5 | Acetyltributyl citrate | 1.0 |
| 6 | Dimethyldistearylammonium hectolite | 0.5 |
| 7 | Butyl acetate | 30.0 |
| 8 | Ethyl acetate | 10.0 |
| 9 | Isopropyl alcohol | 5.0 |
| 10 | Iron oxide-laden silicone resin-coated silicone elastomer composite particles of Example 2 | appropriate |
| | Total | 100.0 |

*Acrylic silicone resin: KP-549 by Shin-Etsu Chemical Co., Ltd.
**Methyl trimethicone: TMF-1.5 by Shin-Etsu Chemical Co., Ltd.

Preparation Procedure

A: Ingredients 7 to 9 were mixed, to which ingredients 4 to 6 were added and mixed until uniform.

B: Ingredients 1 to 3 were added to A and the contents were mixed.

C: Ingredient 10 was added to B and the contents were mixed, obtaining a nail enamel.

The nail enamel thus obtained was lightly spreadable, gave a visually smooth appearance, had water resistance and oil resistance, and lasting cosmetic quality. An enamel coating caused neither a feeling of nail oppression nor nail yellowing, showed no changes with temperature and time, and remained highly stable.

Japanese Patent Application No. 2009-257867 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. Silicone composite particles comprising: 100 parts by weight of spherical particles of a silicone elastomer having a volume average particle size of 0.1 to 100 m, coated on their surfaces with 0.5 to 25 parts by weight of a silicone resin based on organosilsesquioxane units, said silicone resin containing 0.1 to 25 parts by weight of inorganic nano-particles having a volume average particle size of up to 100 nm, wherein said inorganic nano-particles are selected from the group consisting of titanium oxide, iron oxide, and zinc oxide, wherein the inorganic nano-particles are dispersed in the silicone, and said silicone composite particles are prepared by adding an acidic or basic substance and a compound selected from the group consisting of alkoxysilanes, silanol-containing silanes and partial condensates thereof to a mixed water dispersion of silicone elastomer spherical particles and inorganic nano-particles, and subjecting the compound to hydrolytic condensation reaction, thereby coating surfaces of the silicone elastomer spherical particles with a silicone resin having the inorganic nano-particles laden therein while taking inorganic nanoparticles therein.

2. A method for preparing silicone composite particles of the method comprising the steps of: adding an acidic or basic substance and a compound selected from the group consisting of alkoxysilanes, silanol-containing silanes and partial condensates thereof, to a mixed water dispersion of silicone elastomer spherical particles and inorganic nano-particles, and subjecting the compound to hydrolytic condensation reaction, thereby coating surfaces of the silicone elastomer spherical particles with a silicone resin having the inorganic nano-particles laden therein so as to obtain silicone composite particles, wherein
the silicone composite particles comprise 100 parts by weight of spherical particles of a siliconeelastomer having a volume average particle size of 0.1 to 100 um, coated on their surfaces with 0.5 to 25 parts by weight of a silicone resin based on organosilsesquioxane units, said silicone resin containing 0.1 to 25 parts by weight of inorganic nano-particles having a volume average particle size of up to 100 nm, wherein said inorganic nano-particles are selected from the group consisting of titanium oxide, iron oxide, and zinc oxide, and the inorganic nano-particles are dispersed in the silicone resin.

3. A cosmetic composition comprising the silicone composite particles of claim 1.

4. A UV screen cosmetic composition comprising: silicone composite particles comprising 100 parts by weight of spherical particles of a silicone elastomer having a volume average particle size of 0.1 to 100 pm, coated with 0.5 to 25 parts by weight of a silicone resin based on organosilsesquioxane units, said silicone resin containing 0.1 to 25 parts by weight of inorganic nano-particles having a volume average particle size of up to 100 nm, wherein said inorganic nano-particles are selected from the group consisting of titanium oxide, iron oxide and zinc oxide, wherein the inorganic nano-particles are dispersed in the silicone resin, and said silicone composite particles are prepared by adding an acidic or basic substance and a compound selected from the group consisting of alkoxysilanes, silanol-containing silanes and partial condensates thereof to a mixed water dispersion of silicone elastomer spherical particles and inorganic nano-particles, and subjecting the compound to hydrolytic condensation reaction, thereby coating surfaces of the silicone elastomer spherical particles with a silicone resin having the inorganic nano-particles laden therein while taking inorganic nanoparticles therein.

5. The silicone composite particles of claim 1, wherein the content of inorganic nano-particles is 0.1 to 7.3 parts by weight relative to 100 parts by weight of the silicone elastomer.

6. Silicone composite particles comprising:
100 parts by weight of spherical particles of a silicone elastomer having a volume average particle size of 0.1 to 100 μm, coated on their surfaces with 0.5 to 25 parts by weight of a silicone resin based on organosilsesquioxane units, said silicone resin containing $1\times10^5$ to $1\times10^{-2}$ parts by weight of inorganic nano-particles of silver having a volume average particle size of up to 100 nm, wherein the inorganic nano-particles are dispersed in the silicone resin, and
said silicone composite particles are prepared by
adding an acidic or basic substance and a compound selected from the group consisting of alkoxysilanes, silanol-containing silanes and partial condensates thereof to a mixed water dispersion of silicone elastomer spherical particles and inorganic nano-particles, and
subjecting the compound to hydrolytic condensation reaction, thereby coating surfaces of the silicone elastomer spherical particles with a silicone resin having the inorganic nano-particles laden therein while taking inorganic nanoparticles therein.

7. A method for preparing silicone composite particles of, the method comprising the steps of: adding an acidic or basic substance and a compound selected from the group consisting of alkoxysilanes, silanol containing silanes and partial condensates thereof, to a mixed water dispersion of silicone elastomer spherical particles and inorganic nano-particles, and subjecting the compound to hydrolytic condensation reaction, thereby coating surfaces of the silicone elastomer spherical particles with a silicone resin having the inorganic nano-particles laden therein so as to obtain silicone composite particles, wherein the silicone composite particles comprise 100 parts by weight of spherical particles of a silicone elastomer having a volume average particle size of 0.1 to 100 um, coated on their surfaces with 0.5 to 25 parts by weight of a silicone resin based on organosilsesquioxane units, said silicone resin containing $1\times10^5$ to $1\times10^{-2}$ parts by weight of inorganic nano-particles of silver having a volume average particle size of up to 100 nm, and the inorganic nano-particles are dispersed in the silicone resin.

8. A cosmetic composition comprising the silicone composite particles of claim 6.

9. A deodorant cosmetic composition comprising silicone composite particles comprising 100 parts by weight of spherical particles of a silicone elastomer having a volume average particle size of 0.1 to 100 pm, coated with 0.5 to 25 parts by weight of a silicone resin based on organosilsesquioxane units, said silicone resin containing $1\times10^5$ to $1\times10^{-2}$ parts by weight of inorganic nano-particles of silver having a volume average particle size of up to 100 nm, wherein the nanoparticles are dispersed in the silicone resin, and said silicone composite particles are prepared by adding an acidic or basic substance and a compound selected from the group consisting of alkoxysilanes, silanol-containing silanes and partial condensates thereof to a mixed water dispersion of silicone elastomer spherical particles and inorganic nano-particles, and subjecting the compound to hydrolytic condensation reaction, thereby coating surfaces of the silicone elastomer spherical particles with a silicone resin having the inorganic nano-particles laden therein while taking inorganic nanoparticles therein.

10. The cosmetic composition of claim 3, configured as a UV screen cosmetic composition, comprising 0.5 to 10.0% by weight of said silicone composite particles.

11. The cosmetic composition of claim 8, configured as a deodorant cosmetic composition, comprising 0.1 to 10.0% by weight of said silicone composite particles.

12. The silicone composite particles of claim 1, wherein the silicone elastomer comprises linear organosiloxane blocks having the chemical formula:

$$-(R^1{}_2SiO_{2/2})_n-$$

wherein $R^1$ is a substituted or unsubstituted monovalent hydrocarbon group of 1 to 30 carbon atoms and n is a positive number of 5 to 5,000.

13. The silicone composite particles of claim 1, wherein the silicone elastomer is a cured product of curable liquid silicone composition (1) or (2),
wherein liquid silicone composition (1) comprises:
(A1) an organopolysiloxane having at least 2 monovalent olefinic unsaturated groups in the molecule of the average formula $$R^2{}_aR^3{}_bSiO_{(4-a-b)/2}$$

wherein $R^2$ is a substituted or unsubstituted monovalent hydrocarbon group of 1 to 30 carbon atoms free of aliphatic unsaturation, $R^3$ is a monovalent olefinic unsaturated group of 2 to 6 carbon atoms, and the subscripts a and b are positive numbers in the range of 0<a<3, 0<b≤3, and 0.1≤a+b≤3;
(B1) an organohydrogenpolysiloxane having at least 3 silicon-bonded hydrogen atoms in the molecule of the average formula $$R^4{}_cH_dSiO_{(4-c-d)/2}$$

wherein $R^4$ is a substituted or unsubstituted monovalent hydrocarbon group of 1 to 30 carbon atoms free of aliphatic unsaturation and the subscripts c and d are positive numbers in the range of 0<c<3, 0<d≤3, and 0.1≤c+d≤3,
provided that a combination of (A1) and (B1) are present in such a proportion as to provide 0.5 to 2 hydrosilyl groups per monovalent olefinic unsaturated group; and
(C) a platinum base catalyst, and
wherein liquid silicone composition (2) comprises:
(A2) an organopolysiloxane having at least 3 monovalent olefinic unsaturated groups in the molecule of the average formula $$R^2{}_aR^3{}_bSiO_{(4-a-b)/2}$$

wherein $R^2$ is a substituted or unsubstituted monovalent hydrocarbon group of 1 to 30 carbon atoms free of aliphatic unsaturation, $R^3$ is a monovalent olefinic unsaturated group of 2 to 6 carbon atoms, and the subscripts a and b are positive numbers in the range of 0<a<3, 0<b≤3, and 0.1≤a+b≤3;
(B2) an organohydrogenpolysiloxane having at least 2 silicon-bonded hydrogen atoms in the molecule of the average formula $$R^4{}_cH_dSiO_{(4-c-d)/2}$$

wherein $R^4$ is a substituted or unsubstituted monovalent hydrocarbon group of 1 to 30 carbon atoms free of aliphatic unsaturation and the subscripts c and d are positive numbers in the range of 0<c<3, 0<d≤3, and 0.1≤c+d≤3,
provided that a combination of (A2) and (B2) are present in such a proportion as to provide 0.5 to 2 hydrosilyl groups per monovalent olefinic unsaturated group; and
(C) a platinum base catalyst.

14. The silicone composite particles of claim 1, wherein the silicone resin is a copolymer comprising structural units of one or more types selected from $[R^5SiO_{3/2}]$, $[R^5{}_2SiO_{2/2}]$, $[R^5{}_3SiO_{1/2}]$, and $[SiO_{4/2}]$, wherein each $R^5$ is independently a monovalent organic group of 1 to 20 carbon atoms, $[R^5SiO_{3/2}]$ units being present in said copolymer in an amount of at least 80 mol %.

15. The silicone composite particles of claim 6, wherein the silicone elastomer comprises linear organosiloxane blocks having the formula $$-(R^1{}_2SiO_{2/2})_n-$$

wherein $R^1$ is a substituted or unsubstituted monovalent hydrocarbon group of 1 to 30 carbon atoms, and n is a positive number of 5 to 5,000.

16. The silicone composite particles of claim 6, wherein the silicone elastomer is a cured product of curable liquid silicone composition (1) or (2)
wherein liquid silicone composition (1) comprises:
(A1) an organopolysiloxane having at least 2 monovalent olefinic unsaturated groups in the molecule of the average formula $$R^2{}_aR^3{}_bSiO_{(4-a-b)/2}$$

wherein $R^2$ is a substituted or unsubstituted monovalent hydrocarbon group of 1 to 30 carbon atoms free of aliphatic unsaturation, $R^3$ is a monovalent olefinic unsaturated group of 2 to 6 carbon atoms, and the subscripts a and b are positive numbers in the range of 0<a<3, 0<b≤3, and 0.1≤a+b≤3;
(B1) an organohydrogenpolysiloxane having at least 3 silicon-bonded hydrogen atoms in the molecule of the average formula $$R^4{}_cH_dSiO_{(4-c-d)/2}$$

wherein $R^4$ is a substituted or unsubstituted monovalent hydrocarbon group of 1 to 30 carbon atoms free of aliphatic unsaturation and the subscripts c and d are positive numbers in the range of 0<c<3, 0<d≤3, and 0.1≤c+d≤3,
provided that a combination of (A1) and (B1) are present in such a proportion as to provide 0.5 to 2 hydrosilyl groups per monovalent olefinic unsaturated group; and
(C) a platinum base catalyst, and
wherein liquid silicone composition (2) comprises:
(A2) an organopolysiloxane having at least 3 monovalent olefinic unsaturated groups in the molecule of the average formula $$R^2{}_aR^3{}_bSiO_{(4-a-b)/2}$$

wherein $R^2$ is a substituted or unsubstituted monovalent hydrocarbon group of 1 to 30 carbon atoms free of aliphatic unsaturation, $R^3$ is a monovalent olefinic unsaturated group of 2 to 6 carbon atoms, and the subscripts a and b are positive numbers in the range of 0<a<3, 0<b≤3, and 0.1≤a+b≤3;
(B2) an organohydrogenpolysiloxane having at least 2 silicon-bonded hydrogen atoms in the molecule of the average formula $$R^4{}_cH_dSiO_{(4-c-d)/2}$$

wherein $R^4$ is a substituted or unsubstituted monovalent hydrocarbon group of 1 to 30 carbon atoms free of aliphatic unsaturation and the subscripts c and d are positive numbers in the range of 0<c<3, 0<d≤3, and 0.1≤c+d≤3, provided that a combination of (A2) and (B2) are present in such a proportion as to provide 0.5 to 2 hydrosilyl groups per monovalent olefinic unsaturated group; and (C) a platinum base catalyst.

17. The silicone composite particles of claim 6, wherein the silicone resin is a copolymer comprising structural units of one or more types selected from $[R^5SiO_{3/2}]$, $[R^5_2SiO_{2/2}]$, $[R^5_3SiO_{1/2}]$, and $[SiO_{4/2}]$, wherein each $R^5$ is independently a monovalent organic group of 1 to 20 carbon atoms, $[R^5SiO_{3/2}]$ units being present in said copolymer in an amount of at least 80 mol %.

* * * * *